US007812151B2

(12) United States Patent
Oreste et al.

(10) Patent No.: US 7,812,151 B2
(45) Date of Patent: Oct. 12, 2010

(54) LOW MOLECULAR WEIGHT POLYSACCHARIDES HAVING ANTITHROMBOTIC ACTIVITY

(75) Inventors: Pasqua Anna Oreste, Milan (IT); Giorgio Zoppetti, Milan (IT)

(73) Assignee: Glycores 2000 S.R.L., Milan (IT)

(*) Notice: Subject to any disclaimer, the term of this patent is extended or adjusted under 35 U.S.C. 154(b) by 0 days.

(21) Appl. No.: 10/582,687

(22) PCT Filed: Dec. 15, 2004

(86) PCT No.: PCT/IB2004/004128

§ 371 (c)(1),
(2), (4) Date: Jun. 13, 2006

(87) PCT Pub. No.: WO2005/058976

PCT Pub. Date: Jun. 30, 2005

(65) Prior Publication Data

US 2007/0155694 A1    Jul. 5, 2007

(30) Foreign Application Priority Data

Dec. 17, 2003   (IT)   ........................... MI2003A2498

(51) Int. Cl.
*C08B 37/00*   (2006.01)
*C07H 5/04*    (2006.01)
*C07H 5/06*    (2006.01)
*A61K 31/727*  (2006.01)

(52) U.S. Cl. .......................... 536/54; 536/55.3; 514/56

(58) Field of Classification Search ...................... None
See application file for complete search history.

(56) References Cited

U.S. PATENT DOCUMENTS

| 4,369,256 | A | 1/1983 | Casu et al. |
| 4,411,796 | A | 10/1983 | Casu et al. |
| 5,110,918 | A | 5/1992 | Casu et al. |
| 5,314,876 | A | 5/1994 | Lormeau et al. |
| 5,958,899 | A | 9/1999 | Zoppetti et al. |
| 6,162,797 | A | 12/2000 | Zoppetti et al. |
| 6,288,044 | B1 | 9/2001 | Zoppetti et al. |
| 6,777,398 | B2 | 8/2004 | Zoppetti et al. |
| 6,992,183 | B2 | 1/2006 | Oreste et al. |
| 7,268,122 | B2 | 9/2007 | Zoppetti et al. |
| 2002/0062019 | A1 | 5/2002 | Oreste et al. |
| 2003/0023079 | A1 | 1/2003 | Oreste et al. |
| 2003/0100534 | A1 | 5/2003 | Zoppetti et al. |
| 2004/0077848 | A1 | 4/2004 | Oreste et al. |
| 2004/0146994 | A1 | 7/2004 | Zoppetti et al. |
| 2005/0004358 | A1 | 1/2005 | Oreste et al. |
| 2005/0009780 | A1 | 1/2005 | Zoppetti et al. |
| 2005/0027117 | A1 | 2/2005 | Oreste et al. |
| 2005/0142194 | A1 | 6/2005 | Nocelli et al. |
| 2005/0215518 | A1 | 9/2005 | Oreste et al. |
| 2005/0245736 | A1 | 11/2005 | Oreste et al. |
| 2005/0256079 | A1 | 11/2005 | Oreste et al. |
| 2006/0014718 | A1 | 1/2006 | Oreste et al. |
| 2006/0281152 | A1 | 12/2006 | Zoppetti et al. |
| 2007/0155694 | A1 | 7/2007 | Oreste et al. |

FOREIGN PATENT DOCUMENTS

| WO | 97/43317 | 11/1997 |
| WO | 02/50125 | 6/2002 |
| WO | 02/068477 | 9/2002 |
| WO | 03/106504 | 12/2003 |

OTHER PUBLICATIONS

Jacobsson et al. Biochemical Journal, 1979, 179, pp. 77-87.*
Naggi et al., *Toward a Biotechnological Heparin through Combined Chemical and Enzymatic Modification of the Escherichia coli K5 Polysaccharide*, Seminars in Thrombosis and Hemostasis, vol. 27, No. 5, 2001, pp. 437-443, XP008004483.
Østergaard et al. "The effect of low molecular weight heparin on experimental thrombosis and haemostasis—The influence of production method" Thromb. Res. 45:739-749 (1987).
Petitou et al. "Chemical synthesis of glycosaminoglycans: New approaches to antithrombotic drugs" Nature 350 (suppl.):30-33 (1991).

* cited by examiner

*Primary Examiner*—Shaojia Anna Jiang
*Assistant Examiner*—Layla Bland
(74) *Attorney, Agent, or Firm*—Nixon & Vanderhye P.C.

(57) ABSTRACT

Novel depolymerized-LMWepiK5-N,O-sulfates obtainable starting from a LMW-epiK5-N-sulfate prepared by nitrous depolymerization of an epiK5-N-sulfate or by C5-epimerization of a LMW-K5-N-sulfate obtained by nitrous depolymerization of a K5-N-sulfate. A process consists of submitting the starting depolymerized-LMW-epiK5-N-sulfate to four steps: a O-oversulfation, a partila O-desulfation, a 6-O-sulfation and a N-sulfation. The new depolymerized-LMWepiK5-N,O-sulfates present a di- or trisulfated 2,5-anhydromannitol unit at the reducing end of the majority of its chains, have a content of iduronic acid of 40-60%, a sulfation degree of from 2.3 to 2.9 and a mean molecular weight of from about 1,500 to about 12,000. They exhibit a good antithrombotic activity with a low pro-hemorrhagic risk.

25 Claims, 3 Drawing Sheets

Partially O-desulfated

Final product

LOW MOLECULAR WEIGHT POLYSACCHARIDES HAVING ANTITHROMBOTIC ACTIVITY

This application is the US national phase of international application PCT/IB2004/004128 filed 15 Dec. 2004 which designated the U.S. and claims benefit of IT MI2003A002498 filed 17 Dec. 2003, the entire contents of each of which are hereby incorporated by reference.

OBJECT OF THE INVENTION

The present invention concerns novel low molecular weight polysaccharides derived from K5 polysaccharide, having a good activity on the coagulation parameters with a low hemorrhagic risk, useful as medicaments for the regulation of coagulation and for the prevention and the treatment of thrombosis. More particularly, the invention refers to novel LMW-epiK5-N,O-sulfates having a sulfation degree of 2.7-2.9, obtainable by treating novel LMW-epiK5-N-sulfates (in their turn prepared by nitrous depolymerization of epiK5-N-sulfates), with an O-sulfation agent under O-oversulfation conditions, by submitting the LMW-epiK5-amine-O-oversulfate thus obtained to a selective O-desulfation, treating the partially O-desulfatated product thus obtained to a 6-O-sulfation and finally treating the 6-O-resulfated product thus obtained with a sulfating agent under N-sulfation conditions. Furthermore, the invention refers to a process for the preparation of said LMW-epiK5-N,O-sulfates having a sulfation degree of from 2.3 to 2.9 and to new intermediates.

BACKGROUND OF THE INVENTION

The glycosaminoglycans such as heparin, heparan sulfate, dermatan sulfate, chondroitin sulfate and hyaluronic acid are biopolymers that are industrially extracted from various animal organs.

In particular, heparin, mainly obtained by extraction from pig intestinal mucosa or from bovine lung, is a polydispersed copolymer with a molecular weight distribution from approximately 3,000 to approximately 30,000 D consisting of a mixture of chains basically consisting of a uronic acid (glucuronic acid or iduronic acid) and of an amino sugar (glucosamine) linked by $\alpha$-1→4 or $\beta$-1→4 bonds. In heparin, the uronic unit can be O-sulfated in position 2 and the glucosamine unit is N-acetylated or N-sulfated, 6-O-sulfated, and 3-O-sulfated in approximately 0.5% of the glucosamine units present.

The properties and natural biosynthesis of heparin in mammals have been described by Lindahl et al., 1986 in Lane, D. and Lindahl, U. (Editors) "Heparin. Chemical and Biological Properties; Clinical Applications", Edward Arnold, London, Pages 159-190, by Lindahl, U, Feingold D. S. and Rodén L, 1986 TIBS, 11, 221-225 and by Conrad H. E. "Heparin Binding Proteins", Chapter 2: Structure of Heparinoids, Academic Press, 1998. The biosynthesis of heparin occurs starting from its precursor N-acetyl-heparosan consisting of a mixture of chains consisting of the repetitive disaccharide unit glucuronyl-$\beta$-1→4-N-acetylglucosamine. Said precursor undergoes enzymatic modifications which partially hydrolyze the N-acetyl group, replace it with an $SO_3^-$ group, epimerize the carboxyl in position 5 of a part of the glucuronic units, convert them into iduronic units and introduce O-sulfate groups to get a product which, once extracted industrially, has approximately a double number of sulfate groups in respect of the carboxy groups per disaccharide unit. These enzymatic modifications lead, among other things, to the formation of the pentasaccharidic antithrombin III (ATIII) binding region, called active pentasaccharide, which is the structure necessary for the high affinity bond of heparin to ATIII and fundamental for the anticoagulant and antithrombotic activity of heparin. This pentasaccharide, present inside only some of the chains which form heparin, contains a sulfated glucosamine unit in position 3 and a glucuronic acid spaced out between disaccharides containing iduronic acids.

In nature, the formation of the active pentasaccharide is made possible by the epimerization reaction of the carboxyl of a part of the glucuronic units into iduronic units provided by the D-glucuronyl C5-epimerase (C5-epimerization) and by a suitable sulfation which also leads to the introduction of a sulfate group onto the hydroxyl in position 3 of the glucosamine. More particularly, in nature the formation of the active pentasaccharide is made possible by the fact that the C5-epimerization occurs in clusters, i.e. on portions of chains, and extensively, which results in a product that contains more iduronic units than glucuronic ones. Commercial heparin, in fact, contains approximately 70% iduronic units and 30% glucuronic units.

DESCRIPTION OF THE PRIOR ART

It is known that the capsular K5 polysaccharide isolated from *Escherichia coli*, described by Vann W. F. et al., in European Journal of Biochemistry, 1981, 116, 359-364 ("Vann 1981"), consists of a mixture of chains formed of the repetitive disaccharide unit glucuronyl-$\beta$-1→4-N-acetyl glucosamine and therefore shows the same repetitive disaccharide unit (A)

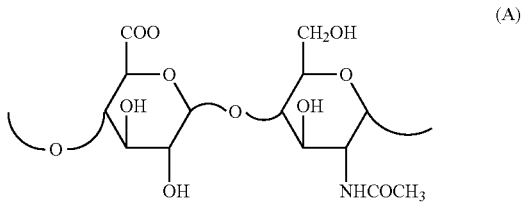

of the N-acetyl-heparosan precursor of heparin. The capsular K5 polysaccharide, herinafter referred to as "K5 polysaccharide" or more simply "K5", was chemically modified by Lormeau et al. as described in U.S. Pat. No. 5,550,116 and by Casu et al. as described in Carbohydrate Research, 1994, 263, 271-284. K5-O-sulfates having antitumoral, antimetastatic, antiviral, in particular anti-HIV, activities are described in EP 333243 and WO 98/34958. The K5 was also modified by chemical and enzymatic means in order to obtain products having the same kind of in vitro biological activity on coagulation as that of heparin as extracted from animal organs (extractive heparin).

The attainment of the products having an activity on coagulation of the same type as that of extractive heparin occurs by processes which mimic that occurring in nature and comprise the key step of C5-epimerization with D-glucuronyl C5 epimerase.

The processes described in IT 1230785, WO 92/17507, WO 96/14425 and WO 97/43317 utilize K5 as starting material. K5 originating from fermentation is subjected to N-deacetylation followed by N-sulfation and, on the K5-N-sulfate thus obtained, by a C5-epimerization with C5-epimerase, obtained either by chromatography of a solution of microsomal enzymes from mouse mastocytoma (IT 1 230

785) or from bovine liver (WO 92/17507, WO 96/14425 and WO 97/43317), is performed in solution.

The D-glucuronyl C5-epimerase from bovine liver was purified by Campbell, P. et al. in J. Biol. Chem., 1994, 269/43, 26953-26958 ("Campbell 1994") who also supplied its composition in amino acids and described its use in solution for the transformation of a K5-N-sulfate into the corresponding 30% epimerized product, demonstrating the formation of iduronic acid by HPLC method following a total nitrous depolymerization up to disaccharide.

The document WO 98/48006 describes the DNA sequence which codes for the D-glucuronyl C5-epimerase and a recombinant D-glucuronyl C-5 epimerase, obtained from a recombinant expression vector containing said DNA, subsequently purified by Campbell et al. as shown by Jin-Ping L. et al. in J. Biol. Chem. 2001, 276, 20069-20077 ("Jin-Ping 2001").

The complete C5-epimerase sequence was described by Crawford B. E. et al. in J. Biol. Chem., 2001, 276(24), 21538-21543 (Crawford 2001).

The document WO 01/72848 describes a method for the preparation of N-deacetylated, N-sulfated derivatives of K5 polysaccharide, epimerized to at least 40% of iduronic acid in respect of the total of the uronic acids, having a molecular weight from 2,000 to 30,000, containing from 25 to 50% of high affinity chains for ATIII and having an anticoagulant and antithrombotic activity, expressed as HCII/antiXa ratio, of from 1.5 to 4.

Said process, which comprises in sequence the preparation of K5 from *Escherichia coli*, N-deacetilation and N-sulfation, C5-epimerization, oversulfation, selective O-desulfation, 6-O-sulfation and N-sulfation, provides a C5 epimerization carried out with C5 epimerase, in solution or immobilized, in the presence of specific bivalent cations. According to the document WO 01/72848, the C5-epimerization can be indifferently carried out with a natural or recombinant enzyme, immobilized o in solution, at a temperature of from 30 to 40° C. for a period of time of from 1 to 24 hours.

Moreover, said document discloses a depolymerization reaction with nitrous acid, carried out on the final product at the end of the above mentioned reaction sequence.

The document US 2002/0062019 describes a process for the preparation of epiK5-N,O-sulfates, active on the regulation of coagulation, having a sulfation degree of from 2.3 to 2.9 and a molecular weight of from 2,000 to 30,000, or from 4,000 to 8,000, or from 18,000 to 30,000. The aforesaid process involves the steps: (s-a) an N-deacetylation of K5 polysaccharide and an N-sulfation of the resulting K5-amine, (s-b) an epimerization of K5-N-sulfate, (s-c) an O-oversulfation of epiK5-N-sulfate, (s-d) a partial O-desulfation, (s-e) a selective 6-O-sulfation, (s-f) an N-sulfation of the product thus obtained, any product obtained at the end of anyone of the steps (s-b)-(s-f) being susceptible to be submitted to depolymerization. Said document describes an epiK5-N,O-sulfate having a molecular weight of 7,400, obtained by the aforesaid steps (s-a)-(s-f) followed by a nitrous depolymerization at the end of step (s-f), with a degree of sulfation from 2.3 to 2.9.

The same document also describes a K5 fraction with a molecular weight of approximately 5,000 which can also be subjected to steps (s-a)-(s-f).

In order to uniform the terminology and render the text more comprehensible, in the present description conventional terms or expressions will be used, in the singular or plural. In particular:

by "K5" or "K5 polysaccharide" is meant the capsular polysaccharide from *Escherichia coli* obtained by fermentation, i.e. a mixture of chains consisting of disaccharide units (A) optionally containing a double bond at the non-reducing end as illustrated above, howsoever prepared and purified according to the methods described in literature, in particular according to Vann 1981, according to Manzoni M. et al., Journal of Bioactive Compatible Polymers, 1996, 11, 301-311 ("Manzoni 1996") or according to the method described in WO 01/72848 or in US 2002/0062019; it is obvious for a person skilled in the art that what is shown hereafter can be applied to any N-acetylheparosan;

by "C5-epimerase" is meant the D-glucuronyl C-5 epimerase, extractive or recombinant, howsoever prepared, isolated and purified, in particular as described in Campbell 1994, in WO 98/48006, in Jin-Ping L. et al. in J. Biol Chem. 2001, 276, 20069-20077 (Jin-Ping 2001") or in Crawford 2001;

by K5-amine is meant at least 95% N-deacetylated K5, preferably fully N-deacetylated, namely in which N-acetyl groups are undetectable with a normal NMR apparatus;

by "K5-N-sulfate" is meant at least 95%, preferably 100%, N-deacetylated and N-sulfated K5, since N-acetyl groups are undetectable with a normal NMR apparatus;

by "epiK5" is meant the K5 and its derivatives in which 40%-60% of the glucuronic units is C5-epimerized to iduronic units by "epiK5-N-sulfate" is meant K5-N-sulfate in which 40%-60% of the glucuronic units is C5-epimerized to iduronic units;

by "epiK5-amine-O-oversulfate" is meant an epiK5-amine-O-sulfate with a sulfation degree of at least 2;

by "epiK5-N,O-sulfate" is meant a K5-N,O-sulfate wherein 40%-60% of the glucuronic units is C5-epimerized to iduronic units, with a sulfation degree of from 2.3 to 2.9;

the conventional terms and expressions hereinabove defined refer to K5 as isolated after fermentation, generally with a molecular weight distribution from approximately 1,500 to approximately 50,000 with a mean molecular weight of 12,000-25,000, advantageously of 15,000-25,000;

unless the molecular weight is otherwise specified, the conventional terms and expressions defined hereinabove, when preceded by the acronym "LMW" (low molecular weight), in particular LMW-epiK5-N-sulfate, LMW-epiK5-amine-O-oversulfate, LMW-epiK5-N,O-sulfate, designate low molecular weight products having a mean molecular weight of from about 1,500 to about 12,000;

when followed by "-derivative", the conventional terms and expressions as defined hereinabove, indicate both the derivatives from native K5 and those of low molecular weight K5, as a whole;

the term "depolymerized-LMW-epiK5-N-sulfate", designates a LMW-epiK5-N-sulfate obtained according to the sequence (i)→(ii) or the sequence (ii)→(i) as illustrated hereinbelow; analogously, the terms "depolymerized-LMW-epiK5-amine-O-oversulfate" and "depolymerized-LMW-epiK5-N,O-sulfate" designate a LMW-epiK5-amine-O-oversulfate and, respectively, a LMW-epiK5-N,O-sulfate obtained starting from a depolymerized-LMW-epiK5-N-sulfate;

the prefix "(epi)", which precedes "K5" in conventional terms and expressions as defined herein above, indicates both the products from native K5 and those from epiK5 (40-60% epimerized), as defined above, as a whole.

Furthermore:

unless otherwise specifically indicated, the term "molecular weight" or "mean molecular weight" indicates the molecular weight determined by HPLC against standard of heparin and low molecular weight heparin;

by the term "approximately" or "about", referring to the molecular weight, is meant the molecular weight measured by viscosimetry±the theoretical weight of a disaccharide unit, including the weight of the sodium, calculated as 461 in the case of an epiK5-N-sulfate-derivative and 644 in the case of a epiK5-N,O-sulfate-derivative with a sulfation degree of 2.8;

by the expression "preponderant species", is meant the compound which, in the mixture constituting the LMW-epiK5-N-sulfate, the LMW-epiK5-amine-O-oversulfate or the LMW-epiK5-N,O-sulfate, is the most represented species, determined by the peak of the curve of the molecular weight measured by HPLC;

unless otherwise specifically stated, by "degree of sulfation" is meant the $SO_3^-/COO^-$ ratio, expressible also as the number of sulfate groups per disaccharide unit, measured by the conductimetric method described by Casu B. et al. in Carbohydrate Research, 1975, 39, 168-176 (Casu 1975);

by "O-oversulfation conditions" is meant an extreme O-sulfation performed, for example, according to the Method C described by B. Casu et al. in Carbohydrate Research, 1994, 263, 271-284 (Casu 1994);

by the term "alkyl" is meant a linear or branched alkyl, whereas "tetrabutylammonium" denotes the tetra(n-butyl) ammonium group.

Finally, it is to be noted that, in the literature, the polysaccharide K5 (K5) is also called "acetylaminoheparosan". Thus, K5-amine corresponds to "aminoheparosan", K5-N-sulfate corresponds to "sulfaminoheparosan", and so on, while, when these products are epimerized, in the literature the above terms are preceded by the term "epimerized". In this context, the present description refers to "K5" in order to emphasize the origin of the products disclosed herein.

SUMMARY OF THE INVENTION

In the patent application PCT/IB03/02338, incorporated herein by reference, there are disclosed epiK5-amine-O-oversulfate-derivatives useful as intermediates in the preparation of epiK5-N,O-oversulfate-derivatives having antiangiogenetic and antiviral activity. Said epiK5-amineO-oversulfate-derivatives are prepared by a process which comprises treating an epiK5-N-sulfate-derivative with, preferably, tetrabutylammonium hydroxide, by letting the reaction mixture to stand for a period of time of 30-60 minutes at a pH of about 7 and isolating the salt, preferably the tetrabutylammonium salt, thus obtained; and treating said salt with an O-sulfating agent under O-oversulfation conditions. The above mentioned document discloses the preparation of LMW-epiK5-amine-O-oversulfates starting from a LMW-epiK5-N-sulfate.

The same document PCT/IB03/02338, as well as the documents IT MI2002A001346 and IT MI2002A001854, also incorporated herein by reference, disclose for the first time LMW-epiK5-N-sulfates, preferably free of N-acetyl groups, wherein the content in iduronic acid in respect of the total of uronic acids is of 40%-60%, preferably around 50%. Said LMW-epiK5-N-sulfates are useful intermediates in the preparation of LMW-epiK5-N,O-sulfates having a high degree of activity on various biological parameters, in particular on coagulation parameters (IT MI2002A001346). The preparation of said LMW-epiK5-N-sulfates is described in detail in the three above documents.

Moreover, PCT/IB03/02339 discloses pharmaceutical compositions comprising, as an active ingredient, an (epi)K5-amine-O-oversulfate-derivative or a pharmaceutically acceptable salt thereof, obtainable by a process which comprises treating an (epi)K5-N-sulfate-derivative, in acidic form, with a tertiary or quaternary organic base, letting the reaction mixture to stand for a period of time of 30-60 minutes, by maintaining the pH of the solution at a value of approximately 7 by addition of said tertiary or quaternary organic base and isolating the salt with said organic base; and treating said organic base salt of said (epi)K5-N-sulfate-derivative with an O-sulfation reagent under O-oversulfation conditions and isolating the (epi)K5-amine-O-oversulfate-derivative.

In preparing N,O-sulfated, N-deacetylated derivatives of K5 polysaccharide, at least 40% epimerized to iduronic acid in respect of the total uronic acids and having low molecular weight as described in WO 01/72848 and in US 2002/0062019, it was observed that the depolymerization of the product of high molecular weight obtained at the end of step (g) of the process described in WO 01/72848 and at the end of step (vi) of the process described in US 2002/0062019 can give non-uniform results since, in general, it affords depolymerized products having a much lower activity on all the coagulation parameters than that of high molecular weight products which they derive from. It is assumed this takes place because degradation with nitrous acid is influenced by the presence of the sulfate groups. In particular the presence of sulfates in position 3 of the glucosamine gives rise to heterogeneous products, as described by Nagasawa et al. in Thrombosis Research, 1992, 65, 463-467 (Nagasawa 1992). In US 2002/0062019, the drawback has been overcome by carrying out the of selective O-desulfation step by maintaining the reaction time of the oversulfated product with dimethyl sulfoxide/methanol in the range of 135-165 minutes, preferably at about 60° C. for 150 minutes. This particular, advantageous method is described in detail in WO 02/50125.

It has now been found that depolymerized-LMW-epiK5-N,O-sulfates having a sulfation degree of from about 2.3 to 2.9 and a good activity on the coagulation parameters can be prepared by submitting a depolymerized-LMW-epiK5-N-sulfate to a an O-oversulfation reaction, for example according to the Method C described by B. Casu et al. in Carbohydrate Research, 1975, 39, 168-176 (Casu 1975) to obtain a depolymerized-LMW-epiK5-amine-O-oversulfate, by submitting the depolymerized-oversulfated product to a selective O-desulfation, then to a 6-O-sulfation and finally by treating the partially desulfated, depolymerized product thus obtained with a sulfating agent under the conditions of an N-sulfation to isolate the desired depolymerized-LMW-epi-K5-N,O-sulfate having a sulfation degree of from about 2.3 to about 2.9.

It has also been found that, by operating starting from a depolymerized-LMW-epiK5-N-sulfate, the selective partial O-desulfation with dimethyl sulfoxide/methanol may be carried out in a more large range of heating times, thus obtaining, in a reproducible manner, final depolymerized-LMW-epiK5-N,O-sulfates having an always high activity on the coagulation parameters, even though variable in function of the selective O-desulfation times employed.

In particular, it has surprisingly been found that, if a depolymerized-LMW-epiK5-N-sulfate having a mean molecular weight of about 6,000 is submitted to an O-oversulfation, the depolymerized-LMW-epiK5-amine-O-oversulfate thus obtained to a selective O-desulfation, the partially O-desulfated depolymerized product to a 6-O-sulfation and then to a N-sulfation under conditions similar to those described in WO 02/50125, a depolymerized-LMW-epiK5-N,O-sulfate is obtained, having a mean molecular weight of about 6,000, a sulfation degree of 2.7-2.9, an anti-Xa activity and an anti-IIa activity both as high as a half of the activity of the low molecular weight heparin Standard (sLMWH), namely an antiXa/anti-IIa ratio identical with that of sLMWH, but a capability of increasing the coagulation time from 5 to 8 times lower than that of sLMWH. Thus, for the first time it has been obtained a glycosaminoglycan derived from the polysaccharide K5 that may be assimilated to the sLMWH as far as the antiXa/anti-IIa ratio is concerned and that, at equal dosages, presents a 2.5- to 4-fold lower hemorrhagic risk than sLMWH.

Furthermore, it has been found that all the depolymerized-LMW-epiK5-amine-O-oversulfates obtainable by the process which comprises the treatment of a depolymerized-LMW-epiK5-N-sulfate with an O-sulfation agent under O-oversulfation conditions, are substantially devoid of anticoagulant activity and have a good microbicidal activity, as that of the LMW-epiK5-amine-O-oversulfates described in PCT/IB03/02339.

Finally, it has been found that all the (epi)K5-amine-O-oversulfate-derivatives having a sulfation degree of from 2 to 4, obtained by treatment of the corresponding (epi)K5-N-sulfate-derivatives with an O-sulfation agent under O-oversulfation conditions, are substantially devoid of anticoagulant activity, have a good microbicidal activity, and thus are active ingredients for the preparation of pharmaceutical compositions. Said pharmaceutical compositions are destined to the treatment of infection of microbial, in particular viral, origin.

DETAILED DESCRIPTION OF THE INVENTION

Figure 1:
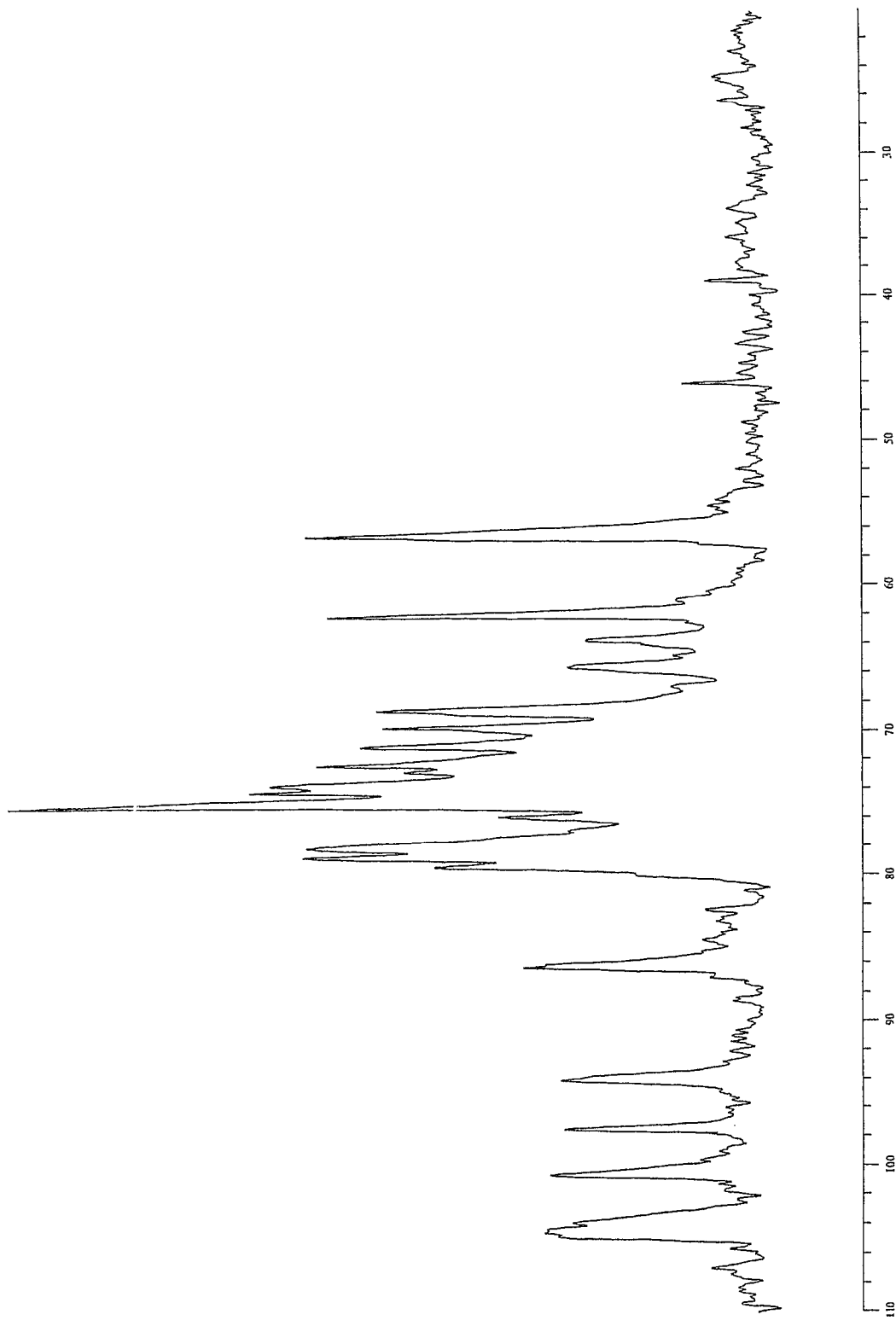
FIG. 1 shows the $^{13}$C-NMR spectrum of the depolymerized-LMW-epiK5-amine-O-sulfate of Example 1(b).

Thus, it is an object of the present invention to provide a process for the preparation of novel depolymerized-LMW-epiK5-N,O-sulfates having a sulfation degree of from 2.3 to 2.9, and of their pharmaceutically acceptable salts, which comprises
(a) treating a tertiary or quaternary organic base salt of a depolymerized-LMW-epiK5-N-sulfate with a sulfation agent under O-oversulfation conditions to obtain a depolymerized-LMW-epiK5-amine-O-oversulfate;
(b) submitting the depolymerized-LMW-epiK5-amine-O-oversulfate thus obtained to a selective O-desulfation to obtain a depolymerized-LMW-epiK5-amine-O-sulfate;
(c) treating a tertiary or quaternary organic base salt of the depolymerized-LMW-epiK5-amine-O-sulfate thus obtained with a O-sulfation agent to obtain a depolymerized-LMW-epiK5-amine-O-sulfate containing at least 80% 6-O-sulfate;
(d) submitting the depolymerized-LMW-epiK5-amine-O-sulfate containing at least 80% 6-O-sulfate thus obtained to a N-sulfation reaction and isolating the depolymerized-LMW-epiK5-N,O-sulfate thus obtained, preferably as the sodium salt thereof which is optionally converted into another pharmaceutically acceptable salt thereof.

Salts with alkaline metals, in particular sodium or potassium, with alkaline-earth metals, in particular calcium and magnesium, with aluminum and with zinc are preferred pharmaceutically acceptable salts.

The starting depolymerized-LMW-epiK5-N-sulfates may be prepared by submitting an epiK5-N-sulfate to a nitrous depolymerization followed by a reduction normally with sodium borohydride. The epiK5-N-sulfates used for the preparation of the above starting depolymerized-LMW-epiK5-N-sulfates are those having an iduronic acid content of 40-60% and contain at least 95% N-sulfate group, as for example those described in WO 01/72848, in US 2002/0062019 or in WO 02/068477.

More particularly, the starting depolymerized-LMW-epiK5-N-sulfates as illustrated above are prepared by a process which comprises submitting a K5-N-sulfate, in any one order,
(i) to a C5-epimerization with a D-glucuronyl C5-epimerase, isolated, purified and in solution or immobilized on a solid support, at a pH of approximately 7, at a temperature of approximately 30° C. and for a time period of 12-24 hours in the presence of at least one bivalent ion selected among calcium, magnesium, barium and manganese; and
(ii) to a nitrous depolymerization followed by a reduction, normally with sodium borohydride.

The expression "in any order" means that the process can indifferently be carried out either in the direction (i)-(ii), i.e. in the sequence shown above, or in the reverse direction (ii)-(i), i. e. by subjecting the K5-N-sulfate at first to the nitrous depolymerization reaction, followed by reduction with sodium borohydride, and then to the C5-epimerization under the aforesaid conditions. The preferred order is in the direction (i)→(ii). The sequence (ii)→(i) is preferably utilized starting from LMW-K5-N-sulfates having a mean molecular weight of more than 4,000, preferably starting from about 6,000. For example, one can determine the amount of sodium nitrite which, starting with 1 g of epiK5-N-sulfate, allows the attainment of a LMW-epiK5-N-sulfate with a mean molecular weight of more than 4,000, in particular of at least 6,000, in order to obtain useful intermediates for the preparation of corresponding LMWepiK5-N,O-sulfates having a sulfation degree of from 2.3 to 2.9. In fact, in this case, in step (ii) the percentage of optimum epimerization is obtained. Thus, when the preparation of the depolymerized-LMW-epiK5-N-sulfate is carried out according to the sequence (ii)→(i), the epimerization occurs in an optimal manner if it is carried out on a depolymerized-LMW-K5-N-sulfate having a mean molecular weight higher than 4,000, advantageously of from 5,000 to 7,500, preferably from 6,000 to 7,500.

The symbols (i) and (ii), as used hereinbelow, designate the depolymerization step and, respectively, the C5-epimerization step, whatever is the order in which these steps are conducted.

The C5-epimerase may be used in solution or immobilized on an inert solid support. In the latter case, the C5-epimerase, preferably recombinant, isolated and purified for example according to Campbell 1994, WO 98/48006, Jin-Ping 2001 or Crawford 2001, is immobilized on an inert support in the presence of the substrate, i.e. in the presence of starting K5-N-sulfate or of LMW-K5-N-sulfate, the latter normally having a mean molecular weight of more than 4,000, advantageously of from 4,000 to 7,500, more advantageously from 5,000 to 7,500, preferably of at least 6,000. The immobilization is performed according to conventional methods, for example as described in WO 01/72848.

The C5-epimerization reaction is carried out by recirculating 20-1,000 ml of a 25 mM HEPES solution at a pH of approximately 7 containing 0.001-10 g of substrate (K5-N-sulfate or LMW-K5-N-sulfate, the latter normally with a mean molecular weight of more than 4,000, in particular from 4,000 to 7,500) and a cation selected among calcium, magnesium, barium and manganese at a concentration of from 10 to 60 mM through a column containing from $1.2 \times 10^7$ to $3 \times 10^{11}$ cpm of the immobilized enzyme, by maintaining the pH at approximately 7 at approximately 30° C., at a flow of 30-220 ml/hour for a period of time of 12-24 hours, advantageously 15-24 hours.

Preferably said solution is recirculated at a flow of approximately 200 ml/hour overnight (15-20 hours). The product obtained is purified and separated according to known methods, for example by ultrafiltration and precipitation with ethanol. The product thus obtained consists either of epiK5-N-sulfate (and in such a case it is dissolved in water and subjected to depolymerization) or of LMW-epiK5-N-sulfate (in such a case it is the end product). The percentage of epimerization, in practice the amount of iduronic units in respect of the glucuronic ones, is calculated by using $^1$H-NMR according to the method described in WO 96/4425.

The nitrous depolymerization reaction is carried out according to known depolymerization methods of heparin, for example according to the method described in EP 37319, in WO 82/03627 or according to the depolymerization method of a K5-N-sulfate described in EP 544592, but starting from a K5-N-sulfate or an epiK5-N-sulfate containing from 0 to no more than 5% acetyl groups. The depolymerization, performed with sodium nitrite and hydrochloric acid on an epiK5-N-sulfate is followed by a reduction in situ with sodium borohydride.

In practice, a cold aqueous solution of (epi)K5-N-sulfate is brought to acid pH (approximately 2) with hydrochloric acid and, still in the cold, treated with sodium nitrite, by maintaining the temperature (approximately 4° C.) and the pH (approximately 2) constant and, upon termination of the depolymerization (approximately 15-30 minutes) the solution is neutralized with sodium hydroxide and treated, still at approximately 4° C., with an aqueous solution of sodium borohydride. Upon termination of the reduction (approximately 4 hours) the excess sodium borohydride is destroyed with hydrochloric acid, the solution is neutralized with sodium hydroxide and the depolymerized (and reduced) product is isolated according to known methods, for example by straightforward precipitation with ethanol or acetone.

The product obtained at the end of the depolymerization can be either a LMW-epiK5-N-sulfate (in such case it constitutes the end product) or a LMW-K5-N-sulfate (and in such case is directly subjected to C5-epimerization as shown hereinabove, after isolation), in particular when it has a mean molecular weight of more than 4,000, advantageously from 4,000 to 7,500, more advantageously from 5,000 to 7,500, preferably of at least 6,000. By appropriately controlling the depolymerization reaction, in particular using different amounts of sodium nitrite/hydrochloric acid, there are obtained LMW-K5-N-sulfates or LMW-epiK5-N-sulfates having a mean molecular weight in the entire interval from approximately 1,500 to approximately 12,000, advantageously from approximately 1,500 to approximately 10,000, preferably from approximately 1,500 to approximately 7,500, calculated at the $^{13}$C-NMR spectrum by the integration of the signal attributed to the C2 of 2,5-anhydromannitol with that of the anomeric carbon of the glucosamine inside the polysaccharide chain.

According to a general manner of procedure, starting for example from 1 g of epiK5-N-sulfate, the starting product is dissolved in 100-200 ml of deionized water and thermostated at 4° C. Then an amount of sodium nitrite is added so as to obtain the desired mean molecular weight. In order to obtain, for example, a LMW-(epi)K5-N-sulfate with a mean molecular weight of from about 2,000 to about 4,000 starting from an (epi)K5-N-sulfate having a mean molecular weight of about 20,000 (measured with the HPLC method equipped with a BioRad BioSil 250 column and using a heparin standard of known molecular weight), there will be required the addition of 330 to 480 mg of sodium nitrite dissolved in a 0.2% aqueous solution. The solution containing the (epi)K5-N-sulfate and the sodium nitrite, kept at 4° C., is brought to pH 2 by addition of 0.1 N HCl cooled to 4° C. It is left to react under slow stirring for 20-40 minutes, then it is neutralized with 0.1 N NaOH. The solution containing the product thus obtained is brought to room temperature and treated with a reducing agent such as for example sodium borohydride (250-500 mg dissolved in 50-100 ml of water) and left to react for 4-8 hours. The excess sodium borohydride is eliminated by bringing the pH to 5-5.5 with 0.1 N HCl and letting the mixture to stand for a further 2-4 hours. At the end, the mixture is neutralized with 0.1 N NaOH and the product is recovered by precipitation with acetone or ethanol after having concentrated the product by evaporation under reduced pressure.

Analogously, the amounts of sodium nitrite can be determined which, starting from 1 g of K5-N-sulfate or epiK5-N-sulfate, allow the attainment of a depolymerized-LMW-K5-N-sulfate or a depolymerized-LMW-epiK5-N-sulfate with a mean molecular weight from about 4,000 to about 12,000, advantageously from about 4,000 to about 7,500, in particular of 6,000-7,500.

The depolymerized-LMW-epiK5-N-sulfates thus obtained, with an iduronic acid content of from 40% to 60%, advantageously of 50-55% and preferably practically free of $NH_2$ and N-acetyl groups, having a mean molecular weight from approximately 1,500 to approximately 12,000, advantageously of from approximately 1,500 to approximately 10,000, preferably from approximately 1,500 to approximately 7,500 and their chemically or pharmaceutically acceptable salts are starting materials in the preparation of the depolymerized-LMW-epiK5-N,O-sulfates of the present invention.

Advantageously, the starting materials in the preparation of the depolymerized-LMW-epiK5-N,O-sulfates of the present invention are depolymerized-LMW-epiK5-N-sulfate-derivatives consisting of a mixture of chains in which at least 90% of said chains have the formula I

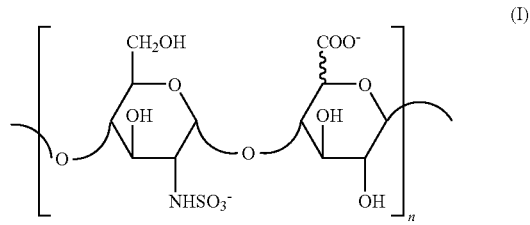

in which 40%-60%, preferably 50%-55% of the uronic units consist of iduronic acid, n is a integer from 2 to 20, advantageously from 3 to 15, and the corresponding cation is a chemically or pharmaceutically acceptable one.

In this context, the term "chemically" refers to a cation usable in chemical synthesis, such as sodium, ammonium, tetra($C_1$-$C_4$)alkylammonium ions, or for the purification of the product.

Advantageous cations are those derived from alkaline metals, alkaline-earth metals, ammonium, tetra($C_1$-$C_4$)alkylammonium, aluminum and zinc. Preferred cations are the sodium, calcium and tetrabutylammonium ions.

The depolymerized-LMW-epiK5-N-sulfates, consisting of a mixture of chains in which at least 90% of said chains have the formula I herein above, obtained by nitrous depolymerization of the corresponding epiK5-N-sulfates shown above and subsequent reduction for example with sodium borohydride, are particularly interesting starting compounds. Among these, depolymerized-LMW-epiK5-N-sulfates consisting of a mixture of chains in which the preponderant species has the formula I'a

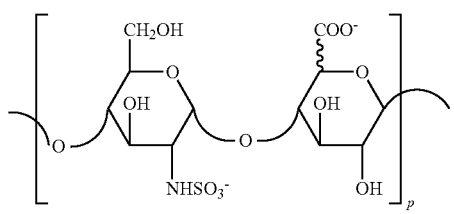

(I'a)

wherein 40%-60% of the uronic units are those of iduronic acid, p is a integer from 4 to 8 and the corresponding cation is a chemically or pharmaceutically acceptable one, are particularly advantageous starting materials. The mean molecular weight of these products is from about 2,000 to about 4,000.

The origin of these epiK5-N-sulfates from a step of nitrous depolymerization followed by a reduction with, for example, sodium borohydride involves, at the reducing end of the majority of the chains in said mixture of chains, the presence of a 2,5-anhydromannitol unit of structure (a)

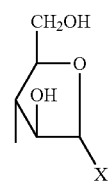

(a)

in which X represents a hydroxymethyl group. Therefore, the reducing end of the majority of the chains is actually represented by the structure (b)

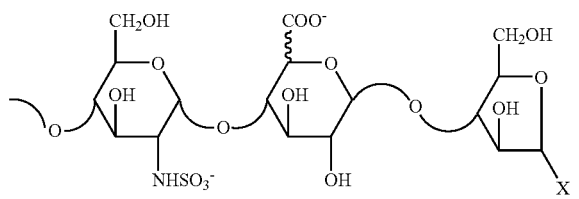

(b)

wherein X is as defined above.

Other particularly advantageous depolymerized-LMW-epiK5-N-sulfates starting materials according to the present invention consist of mixtures of chains in which the preponderant species is a compound of formula I'b

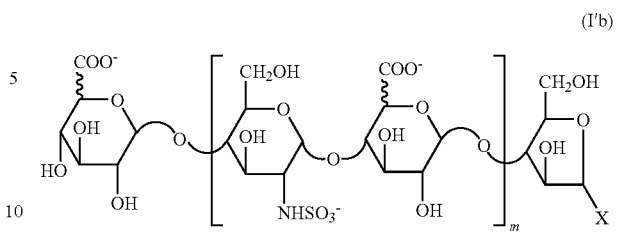

(I'b)

in which X is hydroxymethyl, m is 4, 5 or 6, the corresponding cation is a chemically or pharmaceutically acceptable ion and the glucuronic and iduronic units are present alternately, the non reducing extremity being a glucuronic or iduronic unit. In such a case the glucuronic/iduronic ratio is from 45/55 to 55/45, i.e. approximately 50/50.

The use of the C5-epimerase, preferably recombinant, preferably immobilized on a solid support in the conditions shown above therefore allows not the "cluster" epimerization of K5-N-sulfate-derivatives into epiK5-N-sulfate-derivatives as occurs in nature, but in a regular manner.

In the preparation of the new depolymerized-LMW-epiK5-N,O-sulfates according to the above illustrated process (a)-(d), step (a) consists of an O-oversulfation of the starting depolymerized-LMW-epiK5-N-sulfates, which may be carried out according to anyone of the methods described in the literature, for example according to the Method C described by Casu et al., or according to variations of the same method, for example as described in US 2002/0062019, in order to obtain a depolimerized-LMW-epiK5-amine-O-oversulfate.

The origin of the depolymerized-LMW-epiK5-amine-O-oversulfates from depolymerized-LMW-epiK5-sulfates obtained by nitrous depolymerization and subsequent reduction with, for example, sodium borohydride, involves, at the reducing end of the majority of the chains in said mixture of chains, the presence of a sulfated 2,5-anhydromannitol unit of structure (a')

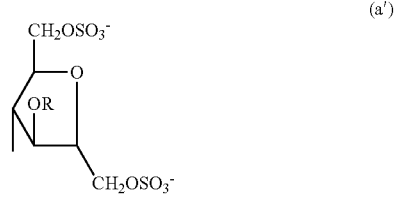

(a')

in which R represents hydrogen or $SO_3^-$.

Thus, the reducing end of the majority of the chains in said mixture of chain is represented by the structure (b')

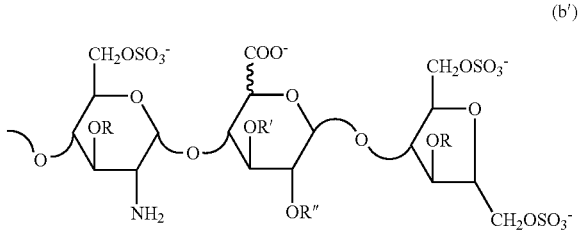

(b')

in which R, R' and R" represent H or $SO_3^-$ and the uronic unit can be glucuronic or iduronic.

By operating as described in US 2002/0062019, a solution containing the depolymerized-LMW-epiK5-N-sulfate at a concentration of 10% is cooled to 10° C. and then passed through a cationic exchange resin IR-120 H$^+$ or an equivalent thereof (35-100 ml). Both the column and the vessel containing the eluate are kept at 10° C. After the passage of the solution, the resin is washed with deionized water until the pH of the permeate is higher than 6 (about 3 volumes of deionized water). The acid solution is brought to neutrality with a tertiary or quaternary organic base such as for example tetrabutyl ammonium hydroxide (15% aqueous solution) to obtain the corresponding ammonium salt. The solution is concentrated to a minimum volume and lyophilized. The obtained product is suspended in 20-500 ml of dimethyl formamide (DMF) or dimethyl sulfoxide (DMSO) and 15-300 g of a sulfating agent, such as the pyridine.$SO_3$ adduct, in solid form or dissolved in DMF or DMSO, are added thereto. The solution is maintained at 20-70° C., preferably at 40-60° C. for 2-24 hours.

A volume of water is added in order to stop the reaction, the pH is brought to neutrality with 1N NaOH. The sample is recovered by precipitation with a saturated solution of NaCl in acetone. The precipitate is separated from the solvent by filtration. The obtained solid is dissolved in 100 ml of deionized water and purified from the residual salts by ultrafiltration. The obtained product shows a sulfate/carboxyl ratio of from 2 to a maximum of 3.2, calculated according to Casu et al. Carbohydate Res. 1975, 39, 168-176. The position 6 of the amino sugar is 80-95% sulfated and the position 2 is not sulfated. The other sulfate groups are present on the position 3 of the amino sugar and in the positions 2 and 3 of the uronic acid.

A depolymerized-LMW-epiK5-amine-O-oversulfate having a higher sulfate/carboxyl ratio, namely of at least 3.4, advantageously of at least 3.5, more advantageously from 3.55 to 4, preferably from 3.55 to 3.8, is obtained by carrying out the above step (a) by (a1) treating a said depolymerized-LMW-epiK5-N-sulfate, in acidic form, with a tertiary or quaternary organic base, letting the reaction mixture to stand for a period of time of 30-60 minutes, maintaining the pH of the solution at a value of about 7 by addition of said tertiary or quaternary organic base and isolating its salt with said organic base;

(a2) treating said organic base salt of said depolymerized-LMW-epiK5-N-sulfate with an O-sulfation agent under O-oversulfation conditions and isolating the depolymerized-LMW-epiK5-amine-O-oversulfate.

The depolimerized-LMW-epiK5-amine-O-oversulfate obtained at the end of step (a) or of the step (a1)+(a2) has a sulfation degree of from 2 to 4 and a mean molecular weight of from about 2,500 to about 12,500, advantageously from about 2,500 to about 10,500, preferably from about 2,500 to about 8,000 and the corresponding cation is chemically or pharmaceutically acceptable.

As it can be noted, notwithstanding the addition of 1-3 $SO_3^-$ groups per disaccharide, starting from a depolymerized-LMW-epiK5-N-sulfate having a mean molecular weight of from about 1,500 to about 12,000, a depolymerized-LMW-epiK5-amine-O-oversulfate with a mean molecular weight of from about 2,500 to about 12,500, namely slightly higher than that of the starting material instead of a theoretical molecular weight range of from about 2,000 to about 15,000, is obtained at the end of step (a). This diminution of the molecular weight is caused by a further depolymerization due to the strongly acidic medium in which step (a) is conducted.

The depolymerized-LMW-epiK5-amine-O-sulfates are advantageously formed of a mixture of chains wherein at least 90% of said chains have the formula II

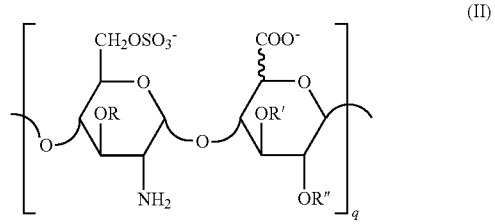

in which 40%-60%, preferably 50%-55%, of the uronic units are those of iduronic acid, R, R' e R" represent hydrogen or a $SO_3^-$ group, for a sulfation degree of from 2 to 4, q is an integer from 2 to 17, advantageously from 2 to 14, preferably from 2 to 11, presents an unit (a') as defined above at the reducing end of the majority of its chains and the corresponding cation is a chemically or pharmaceutically acceptable one.

Depolymerized-LMW-epiK5-amine-O-oversulfates having a very high sulfation degree (at least 3.4, advantageously at least 3.5, more advantageously from 3.55 to 4, preferably from 3.55 to 3.8) obtainable according to the above mentioned steps (a1)+(a2) are formed by a mixture of chains wherein at least 90% of said chains have the formula II wherein 40%-60%, preferably 50%-55% of the uronic units are those of the iduronic acid, R is at least 40%, advantageously 50%-80%, preferably about 65% $SO_3^-$, R' and R" are both $SO_3^-$ or one of them is hydrogen and the other is 5%-10% $SO_3^-$ in glucuronic acid and 10%-15% $SO_3^-$ in iduronic acid, q is as defined above and the corresponding cation is a chemically or pharmaceutically acceptable one.

In step (b) of the process of the present invention, the selective O-desulfation of the depolymerized-LMW-epiK5-amine-O-oversulfate obtained at the end of step (a) is carried out by treatment of the depolymerized-LMW-epiK5-N-sulfate with a mixture DMSO/methanol 9/1, for example according to the methods described by A. Naggi et al., Carbohydrate Research, 2001, 336, 283-290, in WO 01/72848 or in US 2002/0062019.

In practice, a solution of the depolymerized-LMW-epiK5-amine-O-oversulfate obtained at the end of step (a) is passed onto a cationic exchange resin such as IR-120 H$^+$ by washing with deionized water and the percolated solution is brought to pH from 6 to 7 with a tertiary or quaternary organic base such as pyridine. The salt of the depolymerized-LMW-epiK5-amine-O-oversulfate with the organic base, for example its pyridine salt, is isolated by lyophilization of the suitably concentrated solution. The obtained product is treated with a solution dimethysulfoxide/methanol about 9/1 (V/V) and the obtained solution is maintained at 45-90° C. for a period of time of from 1 to 8 hours, advantageously of from 2 to 4 hours, preferably of from 135 to 155 minutes. The partially O-desulfated product, consisting of a depolymerized-LMW-epiK5-amine-O-sulfate partially desulfated prevalently on the primary hydroxyls and on the hydroxyls of the uronic acids, is isolated by precipitation from the solution by addition of deionized water and, subsequently, of acetone, optionally containing sodium chloride in an amount until saturation.

According to a preferred embodiment, the mixture dimethyl sulfoxide/methanol about 9/1 (V/V) is previously heated to the desired temperature, the depolymerized-LMWepiK5-amine-O-oversulfate salt is added thereto and the duration of the O-desulfation reaction is considered starting from the moment in that the whole of the reagents is at the previously selected temperature. The depolymerized-LMW-epiK5-amine-O-sulfate, partially desulfated prevalently on the primary hydroxyls and on the hydroxyls of the uronic acids, is isolated as described above. A little sample may be separated for the characterization and the remaining product is used for the subsequent 6-O-sulfation step (c).

In step (c), the precipitate from acetone is washed with acetone, dissolved in water and the solution is brought to a pH of about 7.5 with 2N NaOH, passed through a IR-120 H$^+$ resin, then neutralized with a tertiary or quaternary organic base such as pyridine or tetrabutyl ammonium hydroxide and the obtained salt is isolated by lyophilization. The 6-O-sulfation is carried out by dissolving the aforesaid salt in DMF and adding the sulfation agent, for example pyridine.$SO_3$, also dissolved in DMF, in an amount of 2.15 grams per gram of product (tetrabutyl ammonium salt). The reaction is carried out by maintaining the mixture at about 0° C. for about 60-120 minutes and the 6-O-sulfated product is isolated by neutralizing the solution with NaOH and by subsequent precipitation with acetone, optionally containing sodium chloride in an amount until saturation. The precipitation operation may be repeated several times. The 6-O-resulfated depolymerized-LMW-epiK5-amine-O-sulfate thus obtained has a 6-O-sulfate content of at least 80%.

In step (d), the 6-O-resulfated depolymerized-LMW-epiK5-O-sulfate is treated with a sulfation agent under the classical N-sulfation conditions. In particular, the operation is carried out by treating an aqueous solution of the 6-O-resulfated depolymerized-LMW-epiK5-O-sulfate obtained at the end of step (c) with sodium carbonate and then with a sulfation agent such as pyridine.$SO_3$ at a temperature of 35-45° C. and the final product, consisting of the depolymerized-LMW-epiK5-N,O-sulfate having a sulfation degree of from 2.3 to 2.9, is isolated as sodium salt, for example by diafiltration. The N-sulfation reaction may be repeated.

The sodium salt of the depolymerized-LMW-epiK5-N,O-sulfate having a sulfation degree of from 2.3 to 2.9 may be converted into another pharmaceutical acceptable salt, such as that of another alkaline metal salt, of an alkaline-earth metal, of aluminum or of zinc according to known methods, for example by ionic exchange with a suitable resin, by precipitation with solvents or by ultrafiltration through suitable membranes. Advantageous salts are those of sodium, potassium, magnesium, calcium, aluminum and zinc. The sodium and calcium salts are preferred.

According to a preferred embodiment, the present invention provides a process for the preparation of depolymerized-LMW-epiK5-N,O-sulfates having a sulfation degree of from 2.3 to 2.9, and of their pharmaceutical acceptable salts, which comprises (ii) submitting a K5-N-sulfate to a nitrous depolymerization to obtain a depolymerized-LMW-K5-N-sulfate having a mean molecular weight higher than 4,000 advantageously from about 5,000 to about 7,500, preferably from about 6,000 to about 7,500;

(i) submitting the depolymerized-LMW-K5-N-sulfate thus obtained to a C5-epimerization with D-glucuronyl-C5-epimerase to obtain a corresponding depolymerized-LMW-epiK5-N-sulfate containing from 40% to 60% iduronic units;

(a) treating a tertiary or quaternary organic base salt of the depolymerized-LMW-epiK5-N-sulfate thus obtained with a sulfation agent under O-oversulfation conditions to obtain a depolymerized-LMW-epiK5-amine-O-oversulfate;

(b) submitting the depolymerized-LMW-epiK5-amine-O-oversulfate thus obtained to a selective O-desulfation to obtain a depolymerized-LMW-epiK5-amine-O-sulfate;

(c) treating a tertiary or quaternary organic base salt of the depolymerized-LMW-epiK5-amine-O-sulfate thus obtained with a O-sulfation agent to obtain a depolymerized-LMW-epiK5-amine-O-sulfate containing at least 80% 6-O-sulfate;

(d) submitting the depolymerized-LMW-epiK5-amine-O-sulfate containing at least 80% 6-O-sulfate thus obtained to a N-sulfation reaction and isolating the depolymerized-LMW-epiK5-N,O-sulfate thus obtained as the sodium salt thereof which is optionally converted into another pharmaceutically acceptable salt.

According to this preferred process, depolymerized-LMW-epiK5-N,O-sulfates having a sulfation degree of from 2.3 to 2.9 and a mean molecular weight of at least 6,000, in particular of from about 6,000 to about 12,000, advantageously from about 6,000 to about 11,000 are obtained.

The depolymerized-LMW-epiK5-N,O-sulfates having a sulfation degree of from 2.3 to 2.9 and their pharmaceutically acceptable salts, obtainable by this preferred process, represent another preferred embodiment of the present invention. The preferred salts are the above mentioned ones, in particular the sodium and calcium salts.

According to a further preferred embodiment, the present invention provides a process which, starting from a K5-N-sulfate, via the sequence (i)→(ii), allows the preparation of depolymerized-LMW-epiK5-N,O-sulfates having a sulfation degree of from 2.3 to 2.9 and a mean molecular weight in the whole range of from about 1,000 to about 12,000.

This process, which is particularly appropriate for the preparation of depolymerized-LMW-epiK5-N,O-sulfates having a very low mean molecular weight (from about 2,000 to about 5,000) not obtainable by the process conducted via the sequence (ii)-(i), comprises (i) submitting a K5-N-sulfate to a C5-epimerization with a D-glucuronyl C5-epimerase isolated, purified and in solution or immobilized on a solid support, at a pH of about 7, at a temperature of about 30° C. and for a period of time of 12-24 hours in the presence of at least one bivalent ion selected among calcium, magnesium, barium and manganese to give an epiK5-N-sulfate have a content of from 40% to 60% in iduronic acid;

(ii) submitting the epiK5-N-sulfate thus obtained to a nitrous depolymerization followed by a reduction, normally with sodium borohydride to obtain a depolymerized-LMW-epiK5-N-sulfate;

(a) treating a tertiary or quaternary organic base salt of the depolymerized-LMW-epiK5-N-sulfate thus obtained with a sulfation agent under O-oversulfation conditions to obtain a depolymerized-LMW-epiK5-amine-O-oversulfate;

(b) submitting the depolymerized-LMW-epiK5-amine-O-oversulfate thus obtained to a selective O-desulfation to obtain a depolymerized-LMW-epiK5-amine-O-sulfate;

(c) treating a tertiary or quaternary organic base salt of the depolymerized-LMW-epiK5-amine-O-sulfate thus obtained with a O-sulfation agent to obtain a depolymerized-LMW-epiK5-amine-O-sulfate containing at least 80% 6-O-sulfate;

(d) submitting the depolymerized-LMW-epiK5-amine-O-sulfate containing at least 80% 6-O-sulfate thus obtained to a N-sulfation reaction and isolating the depolymerized- LMW-epiK5-N,O-sulfate thus obtained as the sodium salt thereof which is optionally converted into another pharmaceutically acceptable salt.

The depolymerized-LMW-epiK5-N,O-sulfates having a sulfation degree of from 2.3 to 2.9 and their pharmaceutical acceptable salts, obtainable by this other preferred process, represent a further preferred embodiment of the present invention. The preferred salts are the above mentioned ones, in particular the sodium and calcium salts.

In particular, according to this further aspect, the present invention refers to novel depolymerized-LMW-epiK5-N,O-sulfates having a sulfation degree of from 2.3 to 2.9, and to their pharmaceutical acceptable salts, having a mean molecular weight of from about 1,500 to about 12,000, but, in particular, lower than 5,000, preferably lower than 4,000, advantageously from about 1,500 to about 5,000, preferably from about 1,500 to about 4,000.

It is to be noted that the molecular weight of the new depolymerized-LMW-epiK5-N,O-sulfates is approximately equal to that of the starting depolymerized-LMW-epiK5-N-sulfates due to the partial depolymerization occurring in the O-oversulfation step (a) or (a1)+(a2).

More particularly, according to its most preferred embodiment, the present invention concerns depolymerized-LMW-epiK5-N,O-sulfates having a sulfation degree of from 2.3 to 2.9, advantageously from 2.5 to 2.9, preferably from 2.7 to 2.9, and a mean molecular weight of from about 1,500 to about 12,000, advantageously from about 1,500 to about 10,000, preferably from about 1,500 to about 8,000 and characterized by the presence of the structure (a') at the reducing end of the majority of its chains, and their pharmaceutically acceptable salts. A depolymerized-LMW-epiK5-N,O-sulfate, or a pharmaceutically acceptable salt thereof, exhibiting an interesting antithrombotic activity, comparable with that of the LMWH but with a 2.5- to 4-fold lower risk to induce bleeding than LMWH does, has a mean molecular weight of about 6,000. Preferably, this depolymerized-LMW-epiK5-N,O-sulfate has a sulfation degree of from 2.7 to 2.9, a content of 80-95% in glucosamine 6-O-sulfate, of 95-100% in glucosamine N-sulfate, of 45-55% in glucosamine 3-O-sulfate, of 35-45% in glucuronic acid 3-O-sulfate, of 15-25% in iduronic acid 2-O-sulfate and presents an unity (a') as defined above at the reducing end of the majority of its chains.

Advantageous depolymerized-LMW-epiK5-N,O-sulfates of the present invention consist of mixtures of chains in which at least 80% of said chains has the formula III

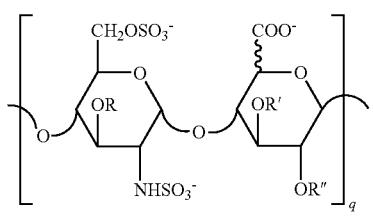

(III)

wherein the uronic units are 40%-60% those of iduronic acid, q is an integer from 2 to 17, advantageously from 2 to 14, preferably from 2 to 11, R, R' and R" are hydrogen or $SO_3^-$, for a sulfation degree of from 2.3 to 2.9, and the reducing end of the majority of the chains in said mixture of chains presents a sulfated 2,5-anidromannitol unit of structure (a')

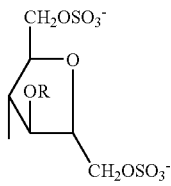

(a')

in which R represents hydrogen or $SO_3^-$, and the corresponding cation is chemically or pharmaceutically acceptable.

A preferred depolymerized-LMW-epiK5-N,O-sulfate, or a pharmaceutically acceptable salt thereof, consists of a mixture of chains in which the preponderant species is a compound of formula III wherein q is 8 or 9, R is 45%-55% $SO_3^-$, R' is 35%-45% $SO_3^-$ in glucuronic acid, R" is 15%-25% $SO_3^-$ in iduronic acid, for a sulfation degree of from 2.7 to 2.9, and presents a sulfated 2,5-anidromannitol unit of structure (a') as defined above at the reducing end of the majority of its chains.

The new depolymerized-LM-epiK5-N,O-sulfates of the present invention possess a very interesting activity on the coagulation parameters. In fact, they have high anti-Xa and anti-IIa activities and involve a very low risk of inducing bleeding in patients in need of a heparinic treatment for the regulation of the coagulation. Depolymerized-LMWepiK5-N,O-sulfates having a mean molecular weight of about 6,000, 95-100% N-sulfated, 80-95% 6-O-sulfated on glucosamine, 45-55% 3-O-sulfated on glucosamine, 35-45% 3-O-sulfated on glucuronic acid, 15-25% 2-O-sulfated on iduronic acid, for a sulfation degree of from 2.7 to 2.9, presenting an unity (a') at the reducing end of the majority of its chains, and their pharmaceutically acceptable salts, are particularly interesting. One of these depolymerized-LMW-epiK5-N,O-sulfates, illustrated hereinbelow in Example 1, has been tested in the classical assays of the anti-Xa and anti-IIa activities, and its effect on the Activated Partial Thromboplastin Time (APTT) has also been tested.

Activity assays used for the determination of the anti-IIa and anti-Xa activities are based on the inhibition of coagulation enzymes by the complex formed by heparin and anti-thrombin III (ATIII). ATIII and factor IIa or factor Xa are added in excess. Residual clotting enzyme reacts with a substrate resulting in a release of spectrophotometrically measurable paranitroaniline, which level is inversely proportional to the level of the clotting enzyme. The used buffers are: 0.9% NaCl in the determination of the anti-Xa activity and Tris 0.05M+NaCl 0.15 M and 1% BSA (Bovine Serum Albumine) in the determination of the anti-IIa activity. The activity of the depolymerized-LMW-epiK5-N,O-sulfate and of the reference compounds (a commercial, unfractionated heparin and a commercial LMWH) were measured against International LMWH standard in terms of anti-Xa and anti-IIa activities. Dilution indicating activity approximately 0.5 U/ml in terms of anti-Xa activity and 0.05 U/ml for anti-IIa activity were determined. A specific activity for unfractionated heparin of 160 U/ml was assumed for calculations.

The effect of the depolymerized-LMW-epiK5-N,O-sulfate of the invention and of the reference products on APTT was measured using IL Test™ APTT Lyophilized Silica Kit. Coagulation is initiated in citrated plasma by adding phospholipids which are required to form complexes which activate Factor X and prothrombin. A contact activator is used to stimulate the production of Factor XIIa by providing a surface for the function of high molecular weight kininogen, kallikrein and Factor XIIa. Calcium is added to trigger further reactions. Time required for clot formation is measured.

In the comparison of the effect of the test and reference compounds on coagulation time, an estimate dose causing coagulation of 100 sec was used. To get this value a dose response curve was prepared using doses causing coagulation times in the range of 50 and 230 seconds. Dose causing a coagulation time af 100 sec was obtained as an estimate from a trendline.

From the aforesaid tests, it resulted that the anti-Xa and anti-IIa activities of the depolymerized-LMW-epiK5-N,O-sulfate of the invention are about 50% of that of LMWH. As a consequence, the depolymerized-LMW-epiK5-N,O-sulfate of the invention, as antithrombotic agent, may be considered as a LMWH with an anti-Xa and anti-IIa of the same order of magnitude.

Also, it resulted that the potency of the depolymerized-LMW-epiK5-N,O-sulfate of the invention in increasing coagulation is weak. In comparison with unfractionated heparin and LMWH, approximately 5-8 fold doses of depolymerized-LMW-epiK5-N,O-sulfate were needed to induce the same effect on APTT.

Thus, the present invention provides, for the first time, a product derived from the polysaccharide K5 that has the same biological characteristics as the sLMWH, but with a lower hemorrhagic risk. The new depolymerized-LMW-epiK5-N,O-sulfates of the present invention, and their pharmaceutically acceptable salts, are thus useful as medicaments for the regulation of coagulation and for the prevention or the treatment of thrombosis as well as active ingredients of pharmaceutical compositions for the above mentioned indications.

According to a further aspect, the present invention provides a pharmaceutical composition comprising, as an active ingredient, a pharmacologically active amount of a depolymerized-LMW-epiK5-N,O-sulfate as illustrated above, in particular a depolymerized-LMW-epiK5-N,O-sulfate having a sulfation degree of from 2.3 to 2.9, a mean molecular weight of from about 1,500 to about 12,000 and presenting the structure (a'), as defined above, at the reducing end of the majority of its chains, or of a pharmaceutically acceptable salt thereof, in admixture with a pharmaceutical carrier.

In the pharmaceutical compositions of the present invention for oral, subcutaneous, intravenous, transdermal, ophthalmic or topical administration, the active ingredients are preferably administered as dosage units, in admixture with the classic pharmaceutical carriers or vehicles.

The dose can amply change in function of age, weight, and health conditions of the patient. This dose comprises the administration of a dosage unit of from 1 to 1,000 mg, advantageously from 10 to 750 mg, preferably from 250 to 500 mg, once to three times per day, by intravenous, subcutaneous, oral, transdermal, ophthalmic or topical route. By parenteral (subcutaneous or intravenous) administration the preferred dose is of from 5 to 100 mg.

Advantageously, the pharmaceutical compositions of the present invention comprise, as an active ingredient thereof, a depolymerized-LMW-epiK5-N,O-sulfate obtainable starting from a K5-N-sulfate, according to the steps (i)→(ii)→(a)-(d) or (ii)→(i)→(a)-(d) of the above illustrated process, or a pharmaceutically acceptable salt thereof. More advantageously, said active ingredient is a depolymerized-LMW-epiK5-N,O-sulfate having a sulfation degree of from 2.3 to 2.9, a mean molecular weight of from about 1,500 to about 12,000 and presents the structure (a') as defined above at the reducing end of the majority of its chains. Preferably, said depolymerized-LMW-epiK5-N,O-sulfate has a mean molecular weight of about 6,000, is 95%-100% N-sulfated, 80%-95% 6-O-sulfated on glucosamine, 45%-55% 3-O-sulfated on glucosamine, 35%-45% 3-O-sulfated on glucuronic acid, 15%-25% 2-O-sulfated on iduronic acid, for a sulfation degree of from 2.7 to 2.9.

According to another of its aspects, the present invention provides a method for the regulation of the coagulation in a mammal, which comprises administering to said mammal in need of said regulation of the coagulation an effective amount of a depolymerized-LMW-epiK5-N,O-sulfate as illustrated above. Moreover, the invention provides a method for preventing or treating thrombosis in a mammal, which comprises administering to said mammal an effective amount of a depolymerized-LMW-epiK5-N,O-sulfate as illustrated above. For the regulation of the coagulation or for preventing or treating thrombosis, the effective amount of depolymerized-LMW-epiK5-N,O-sulfate is of from 5 to 100 mg. Said effective amount is administered in a pharmaceutical composition among those illustrated above. Advantageously, said depolymerized-LMW-epiK5-N,O-sulfate has a sulfation degree of from 2.3 to 2.9, a mean molecular weight of from about 1,500 to about 12,000 and presents the structure (a') as defined above at the reducing end of the majority of its chains.

Preferably, said depolymerized-LMW-epiK5-N,O-sulfate has a mean molecular weight of about 6,000, is 95%-100% N-sulfated, 80%-95% 6-O-sulfated on glucosamine, 45%-55% 3-O-sulfated on glucosamine, 35%-45% 3-O-sulfated on glucuronic acid, 15%-25% 2-O-sulfated on iduronic acid, for a sulfation degree of from 2.7 to 2.9.

Finally, as illustrated hereinabove, all the (epi)K5-amine-O-oversulfate-derivatives having a sulfation degree of from 2 to 4 have microbicidal activity and are active ingredients of pharmaceutical compositions for the treatment of infectious, in particular viral, diseases. Advantageously, said pharmaceutical compositions comprise, as an active ingredient thereof, a pharmacologically effective amount of an (epi)K5-amine-O-oversulfate-derivative, having a sulfation degree of from 2 to 4, obtainable by treating a tertiary or quaternary organic base salt of an (epi)K5-N-sulfate with a sulfation agent under O-oversulfation conditions, or a pharmaceutically acceptable salt thereof, in admixture with a pharmaceutical carrier.

In particular, according to another of its aspects, the invention provides a pharmaceutical composition comprising, as active ingredient, a pharmacologically active amount of an (epi)K5-amine-O-oversulfate-derivative having a sulfation degree of from 2 to 4, or of a pharmaceutically acceptable salt thereof, obtainable by treating a tertiary or quaternary organic base salt of an (epi)K5-N-sulfate-derivative with a O-sulfating agent under O-oversulfation conditions, said (epi)K5-N-sulfate-derivative salt with said organic base having been isolated according to known methods, in particular by lyophilization, immediately after its formation at a pH of from about 5 to about 9, in admixture with a pharmaceutical carrier.

More precisely, the (epi)K5-amine-O-oversulfate-derivative used as active ingredient of the compositions of the present invention is obtainable by (a1') treating an (epi)K5-N-sulfate-derivative, in its acidic form, with a tertiary or quaternary organic base and isolating its salt with said tertiary or quaternary organic base immediately after its formation, at a pH of from about 5 to about 9;

(a2') treating said tertiary or quaternary organic base salt of said (epi)K5-N-sulfate-derivative with an O-sulfation agent under the conditions of an O-oversulfation and isolating the (epi)K5-amine-O-oversulfate-derivative as the sodium salt thereof which can subsequently be converted into another salt.

In the pharmaceutical compositions of the present invention for oral, subcutaneous, intravenous, transdermal, ophthalmic or topical administration, the active ingredients (epi) K5-amine-O-oversulfate-derivatives are preferably administered in the form of dosage units, in mixture with the classic pharmaceutical excipients or vehicles. The dose regimen can vary widely depending on the age, the weight and health condition of the patient. This dose regimen includes the administration of a dose of an (epi)K5-amine-O-oversulfate-derivative from 1 to 1000 mg, advantageously from 10 to 750 mg, preferably 250 to 500 mg from one to three times a day by intravenous, subcutaneous, oral, transdermal, ophthalmic or topical administration.

The pharmaceutical compositions comprising an (epi)K5-amine-O-oversulfate-derivative such as those shown above are formulated with the classic carriers suitable for the different ways of administration. Particularly advantageous are the formulations in the form of creams, ointments, liniments, gels, foams, balsams, vaginal pessaries, suppositories, solutions or suspensions suitable for local administration.

The following examples illustrate the invention.

PREPARATION I (i) Epimerization to epiK5-N-sulfate

Ten grams of K5-N-sulfate obtained as described in Example 2, steps (i) and (ii), of WO 02/068477, the $^1$H-RMN spectrum of which showing no signals relating to acetyl groups or $NH_2$, are dissolved in 600 ml of 25 mM HEPES buffer at pH 7, containing $CaCl_2$ at a concentration of 50 mM and the solution thus obtained is made to recirculate through a 50 ml column filled with Sepharose 4B resin containing 5 g of recombinant C5-epimerase (WO 96/14425) immobilized as described in Example 1 of WO 01/72848. The reaction is carried out at 30° C. at pH 7 with a flow of 200 ml/h for 24 hours. The product obtained is purified by ultrafiltration and precipitation with ethanol. Thus, an epiK5-N-sulfate having an iduronic acid content of 54% is obtained (ii) Depolymerization of epiK5-N-sulfate.

To a solution of 1 g of the product thus obtained, in 25 ml of distilled water, are added 230 mg of sodium nitrite dissolved in 115 ml of distilled water. The solution is then brought to 4° C., the pH is adjusted to 2 with 0.1 N HCl and maintained for 30 minutes. At the end of the reaction the solution is brought to room temperature and the pH to 7 with 0.1 N NaOH. The solution is then added with 450 mg of $NaBH_4$ and left to react for 4 hours. The product is recovered by precipitation with 3 volumes of acetone at 4° C., filtration with filtering funnel and dried at 40° C. in a vacuum oven to give 900 mg of depolymerized-LMW-epiK5-N-sulfate with an iduronic acid content of 54% and a molecular weight distribution from 1,000 to 4,000, measured with HPLC method.

PREPARATION II

Depolymerized-LMW-epiK5-N-sulfate With Mean Molecular Weight of About 5,000. Sequence (ii)→(i)

(ii) Depolymerization of K5-N-sulfate 2 g of K5-N-sulfate, obtained as described in Example 2, steps (i) and (ii), of WO 02/068477, is depolymerized as described in step (ii) of the above PREPARATION I, using 100 mg of sodium nitrite and 300 mg of sodium borohydride. An amount of 1.8 g of depolymerized-LMW-K5-N-sulfate with a mean molecular weight of 5,000 is obtained.

(i) Epimerization of Depolymerized-LMW-K5-N-Sulfate 1 g of depolymerized-LMW-K5 N-sulfate obtained in step (ii) herein above is treated as described in step (i) of PREPARATION I. An epimerized product is obtained with an iduronic acid/glucuronic acid ratio of 44/56 against a ratio of 0/100 of the starting product, with a molecular weight distribution of from 2,000 to 10,000 and with a mean molecular weight of 5,000 D. The yield in depolymerized-LMW-epiK5-N-sulfate, calculated by measuring the content of uronic acids against standard with the carbazole method (Bitter and Muir, Anal. Biochem. 1971, 39, 88-92) is 90%.

PREPARATION III

Depolymerized-LMW-epiK5-N-sulfate. Sequence (i)→(ii)

(i) Epimerization of K5-N-sulfate

A 2 g amount of K5-N-sulfate, obtained as described in Example 2, steps (i) and (ii), of WO 02/068477, is dissolved in 120 ml of 25 mM HEPES buffer, pH 7, containing 50 mM $CaCl_2$. The solution obtained is made to recirculate through a 50 ml column filled with the resin containing the immobilized enzyme obtained as described in WO 96/14425. This operation is carried out at 30° C. with a flow of 200 ml/h for 24 hours. The product obtained is purified by ultrafiltration through a 1000 D membrane and passing over an IR 120 H$^+$ ionic exchange column, neutralizing the eluate with 1N NaOH. The sample is recovered by precipitation with ethanol or acetone. An epimerized product is obtained with an iduronic acid/glucuronic acid ratio of 55/45 against a ratio of 0/100 of the starting product. The percentage of epimerization was calculated with $^1$H-RMN according to the method described in WO 96/14425. The yield in epiK5-N-sulfate, calculated by measuring the content of uronic acids against a standard with the carbazole method (Bitter and Muir Anal. Biochem. 39, 88-92-1971) is 90%.

(ii) Depolymerization of epiK5-N-sulfate

One gram of product obtained in step (a) is depolymerized by the degradation method with nitrous acid and subsequent reduction of the aldehyde which forms. In particular the operation is conducted by dissolving the product in 25 ml of distilled water and adding it with 230 mg of sodium nitrite dissolved in 115 ml of distilled water. The solution is then brought to 4° C. and the pH to 2 with 0.1 N HCl and maintained for 30 minutes. At the end of the reaction the solution is brought to room temperature and the pH to 7 with 0.1 M NaOH. The solution is then added with 450 mg. of $NaBH_4$ and left to react for 4 hours. The product is recovered by precipitation with 3 volumes of acetone at 4° C., filtration with filtering funnel and dried at 40° C. in a vacuum oven to give 900 mg of depolymerized-LMW-epiK5-N-sulfate with a molecular weight distribution measured with HPLC method which ranges from 1,000 to 4,000 and with a glucuronic unit content of 45% and an iduronic unit content of 55%.

PREPARATION IV

Depolymerized-LMW-epiK5-N-sulfate Having a Mean Molecular Weight of About 2,000

To a solution of 1 g of epiK5-N-sulfate, obtained as described in Example 12, paragraphs [0251]-[0265] of US 2002/0062019, in 200 ml of distilled water, 480 mg of sodium nitrite dissolved in 240 ml of distilled water are added. The solution is then brought to 4° C., the pH is adjusted to 2 with 0.1 N HCl and maintained for 30 minutes. At the end of the reaction the solution is brought to pH 7 with 0.1 M NaOH and then to room temperature. The solution is then added with 450 mg. of NaBH$_4$ and reacted for 4 hours. The excess NaBH$_4$ is eliminated by adjusting the pH to 5-6 with HCl. The product, neutralized with 0.1 M NaOH, is recovered by precipitation with 3 volumes of acetone at 4° C., filtration with filtering funnel and dried at 40° C. in a vacuum oven. 900 mg of depolymerized-LMW-epiK5-N-sulfate are obtained with a mean molecular weight of approximately 2,000, consisting of a mixture of chains in which the preponderant species is a compound of formula I'b in which m is 4.

PREPARATION V

Depolymerized-LMW-epiK5-N-sulfate With Man Molecular Weight of 6.000

Starting K5-N-sulfate

A solution of 8 g of 95% pure K5 in 800 ml of 2N NaOH is heated to 60° C. for 24 hours. After cooling, the solution is brought to pH 7 by 6N HCl. To the thus neutralized solution, at first 12.8 g of sodium carbonate, then, portionwise in 4 hours, 12.8 g of pyridine.SO$_3$ adduct in solid form are added. The reaction mixture is kept at 40° C. for 24 hours. After elimination of the salts by ultrafiltration on membrane Millipore Prepscale TFF 1000 D cut-off, the obtained product is recovered by precipitation with 3 volumes of acetone. Thus, 8 g of K5-N-sulfate are obtained. Its $^1$H-NMR spectrum shows a 100% N-sulfation (absence of signals due to NH$_2$ and acetyl groups).

Depolymerized-LMW-epi-K5-N-sulfate. Sequence (i)→(ii)

(i) Epimerization.

The 8 g of K5 N-sulfate thus obtained are dissolved in 200 ml di Hepes 0.25M pH 7 buffer containing 50 mM CaCl$_2$ and treated in solution with 9.6×10$^{10}$ cpm of recombinant C5-epimerase at 30° C. for 24 hours at pH 7. At the end of the reaction, the sample is purified by elimination of the salts by ultrafiltration on Millipore Prepscale TFF 1000 D cut-off membrane and, then, precipitated with 3 volumes of acetone. Thus, 7.5 g of epiK5-N-sulfate are obtained. Its epimerization percentage, in practice the amount of iduronic units in respect of the glucuronic ones, calculated by $^1$H-RMN according to the method described in WO 96/4425, is 52%.

(ii) Depolymerization.

The 7.5 g of epiK5-N-sulfate thus obtained are dissolved in 150 ml water and the solution is thermostated at 4° C., then the pH is brought to 2.2 by previously cooled 1M HCl. To the solution, 431.2 mg of sodium nitrite, corresponding to 21.56 ml of a 2% solution of sodium nitrite in water, are added. The pH is brought to 2.2 again and the reaction mixture is kept at 4° C. for 20 minutes under stirring. After neutralization to pH 7.0 with 6N HCl, 1.35 g of sodium borohydride are added to the solution. The reduction is carried out by keeping the reaction mixture at room temperature for 4 hours, then the excess of reducing agent is destroyed by bringing the pH to 5 with 1N HCl, stirring until disappearance of effervescence. The pH is brought to 7-7.2 again with 1M NaOH. The depolymerized product is recovered by ultrafiltration with Millipore TFF 1000 D cut-off membrane and subsequent precipitation with 3 volumes of acetone. Thus, 7 g of depolymerized-LMW-K5-N-sulfate are obtained. The mean molecular weight of this product, calculated via HPLC, is 6,000 D.

EXAMPLE 1

(a) Oversulfation (a1) Tetrabutylammonium Salt of the Depolymerized-LMW-epi K5-N-sulfate.

A solution of 7 g of depolymerized-LMW-K5-N-sulfate obtained in PREPARATION V in 350 ml water is passed through a column of IR-120 H$^+$. The pH of the eluate is 2.91. The percolated solution is brought to pH 7 with a 15% solution of tetrabutylammonium hydroxide (42.2 ml) and kept one hour at room temperature with controls in order to maintain the pH at a value of 7. After concentration on rotavapor of the tetrabutylammonium salt, the sample is frozen and lyophilized. Thus, 10.9 g of tetrabutylammonium salt of the starting depolymerized-LMW-epiK5-N-sulfate are obtained.

(a2) O-oversulfation.

The tetrabutylammonium salt thus obtained is dissolved in 158 ml of dimethyl formamide, then 28.8 g of pyridine.SO$_3$ dissolved in 158 ml of DMF are added and the reaction mixture is kept at 45° C. for 18 hours. A volume of 316 ml water are added to stop the reaction and the pH is brought to 7 with 30% NaOH. The depolymerized-LMW-epiK5-amine-O-oversulfate is recovered by precipitation with 3 volumes of acetone saturated with NaCl (1.896 liters) and subsequent diafiltration on Millipore TFF 1,000 D membrane until elimination of the salts.

(b) Selective O-desulfation.

The solution containing the depolymerized-LMW-epiK5-amine-O-oversulfate obtained in (a) is passed onto a ion exchange resin IR 120 H$^+$ at room temperature and the pH is brought to 6.7 with pyridine. The solution is then frozen and submitted to lyophilization. The pyridine salt (10.73 g) thus obtained is dissolved in a solution containing 97 ml dimethyl sulfoxide and 11 ml methanol. The pyridine salt of the depolymerized-LMW-epiK5-amine-O-oversulfate is added when the solvent is thermostated at 65°. The reaction beginning is considered when the solvent is at 65° C. and, starting from this moment, the reaction mixture is maintained at this temperature for 2 hours and a half (in a preparation the pH at the end was 2.24). The reaction mixture is cooled by using ice-water to reach about 30° C., then 4.5 ml water are added. The sample is recovered by percolating 5 volumes of acetone into the solution and the precipitate which forms is recovered by filtration on guch G4. The cake is then washed with acetone and then dissolved in water again. The pH is brought to 7.5 with 2 N NaOH. The 300 MHz $^{13}$C-NMR spectrum of the depolymerized-LMW-K5-amine-O-sulfate thus obtained is shown in FIG. 1.

(c) 6-O-Sulfation

The solution is passed onto a IR 120 H$^+$ resin and neutralized with a 15% solution of tetrabutylammonium hydroxide. The salt thus obtained is lyophilized to give 12.34 g of partially O-desulfated product consisting of the tetrabutylammonium salt of the above depolymerized-LMW-K5-amine-O-sulfate. The tetrabutylammonium salt thus obtained is dissolved in 150 ml DMF and 14 g of pyridine.SO$_3$ adduct dissolved in 75 ml DMF are added to the solution. The reaction mixture is kept at 0° C. for 90 minutes, then 110 ml water are added thereto to stop the reaction. The pH of the mixture at the end of the reaction (3.4 in a preparation) is brought to 7.2 by 2N NaOH. The sample is recovered by precipitation with 3 volumes of acetone saturated with NaCl. Some drops of acetone saturated with NaCl are added to favor the precipitation. A white precipitate is formed. In a preparation the operation was repeated twice to obtain 6.8 g of depolymerized-LMW-epiK5-amine-O-sulfate with a content of 80% in 6-O-sulfated glucosamine, 50% in 3-O-sulfated glucosamine, 40% in 3-O-sulfated glucuronic acid and 20% in 2-O-sulfated iduronic acid.

Figure 2:
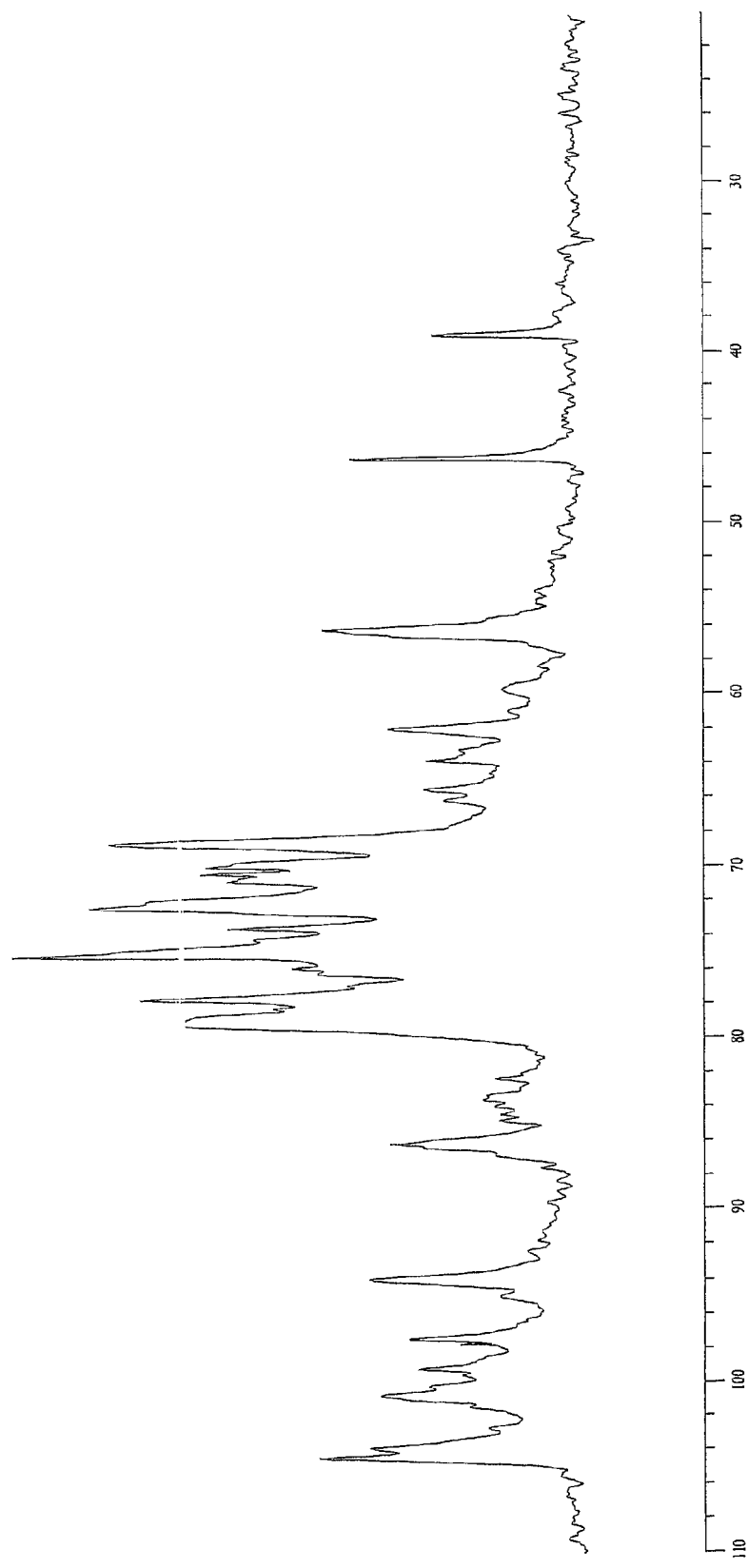
FIG. 2 shows the $^{13}$C-NMR spectrum of the depolymerized-LMW-epiK5-amine-O-sulfate containing at 80% of 6-O-sulfate of Example 1(c).

The 13C-NMR spectrum is shown in FIG. 2.

(d) N-Sulfation

The depolymerized-LMW-epiK5-amine-O-sulfate obtained at the end of step (c) is dissolved in 500 ml water and 12.8 g of sodium carbonate dissolved in 500 ml water are then added to the solution. The pH of the solution after the addition of the carbonate is 10.51. After thermostatting the solution at 40° C., 12.8 g of solid pyridine.SO$_3$ are added thereinto, portionwise and in 4 hours. In a preparation the final pH of the solution was 7.2. The sample is diafiltered in the presence of NaCl and then with water. An amount of 8.0 g of depolymerized-LMW-epiK5-N,O-sulfate with a sulfation degree of 2.83 and a content of 95-100% in N-sulfated glucosamine, of 80% in 6-O-sulfated glucosamine, of 50% in 3-O-sulfated glucosamine, of 40% in 3-O-sulfated glucuronic acid and of 20% in 2-O-sulfated iduronic acid is obtained.

Figure 3:
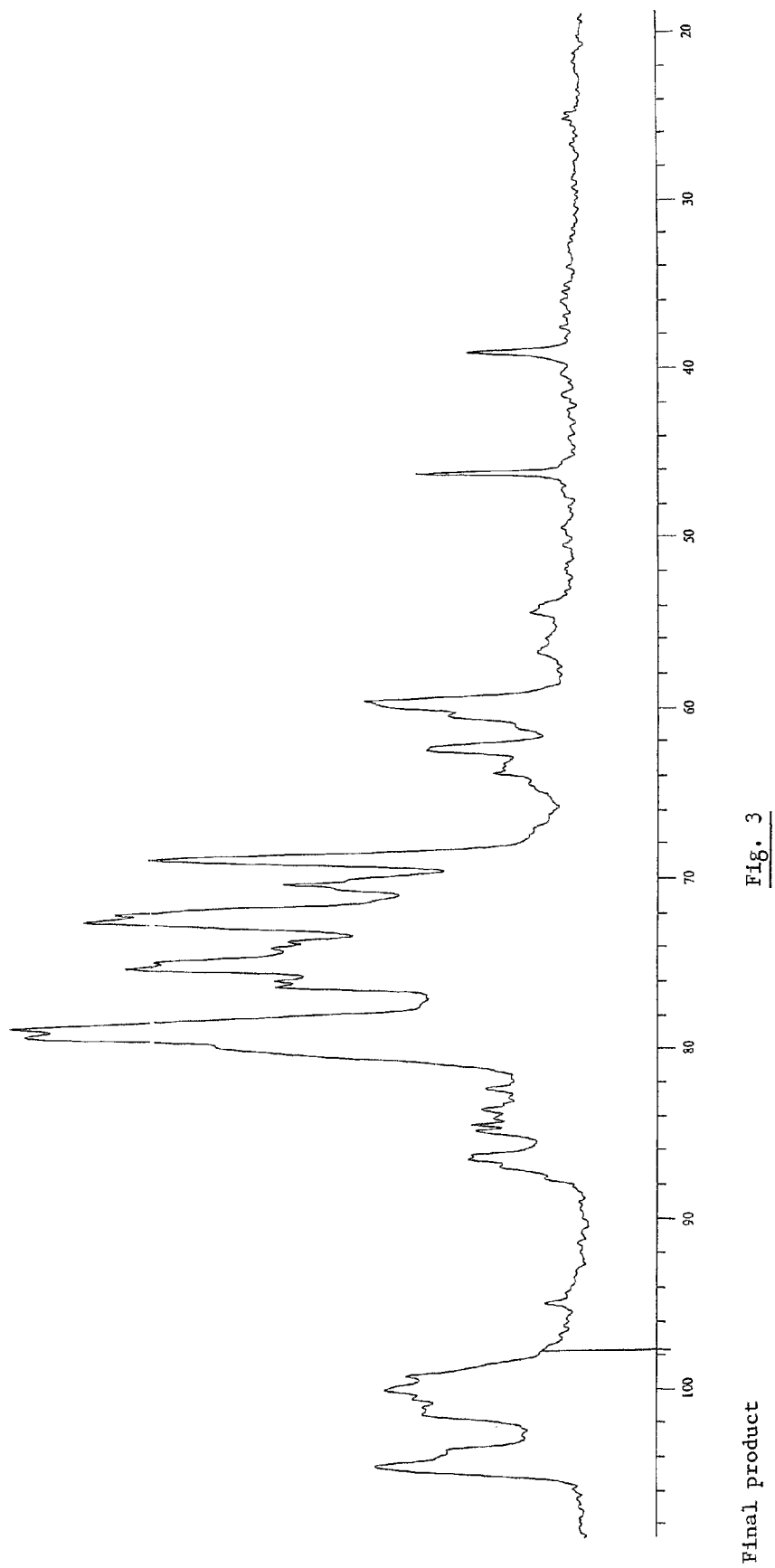
FIG. 3 shows the $^{13}$C-NMRspectrum of the final depolymerized-LMW-epiK5-amine-N,O-sulfate of Example 1(d), indicating the presence of sulfated 2,5-anhydromannitol units.

The $^{13}$C-NMR spectrum of the depolymerized-LMW-epiK5-N,O-sulfate thus obtained is shown in FIG. 3. In the zone between 80 and 90 ppm the signals attributable to the 2, 3 and 4 carbons, typical of the 2,5-anhydromannitol (Casu B., Nouv. Rev. Fr. Hematol., 1984 vol. 26 p. 211-19) are present. The spectrum shows a shift of the signals in the zone between 80 and 90 ppm which indicates the sulfation of the carbon atom in the positions 1, 3 and 6 of said 2,5-anhydromannitol.

EXAMPLE 2

By operating as described in Example 1, by submitting the depolymerized-LMW-K5-N-sulfate with a mean molecular weight of 5,000 obtained in PREPARATION II to an O-oversulfation as in (a), treating the pyridine salt of the LMW-epiK5-amine-O-oversulfate thus obtained with a mixture DMSO/methanol about 9/1 at 70° C. for 150 minutes as in (b), treating the tetrabutylammonium salt of the partially O-desulfated product thus obtained with pyridine.SO$_3$ at 0° C. for 90 minutes as in (c), and finally treating the 6-O-resulfated product first with sodium carbonate and then with pyridine.SO$_3$ as in (d), there is obtained a depolymerized-LMW-epiK5-N,O-sulfate having a mean molecular weight of 5,000, a sulfation degree of 2.8 and a content of 95-100% in N-sulfated glucosamine, of 85% in 6-O-sulfated glucosamine, of 48% in 3-O-sulfated glucosamine, of 38% in 3-O-sulfated glucuronic acid and of 20% in 2-O-sulfated iduronic acid.

The invention claimed is:

1. A process for the preparation of a depolymerized-LMW-epiK5-N,O-sulfate containing 40%-60% iduronic units, containing at least 40% 3-O-sulfate groups in glucosamine units, having a sulfation degree of from 2.3 to 2.9 and characterized by the structure (a')

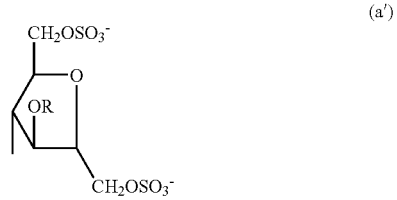

in which R represents hydrogen or SO$_3$⁻ at the reducing end of the majority of its chains, which comprises (a) treating a tertiary or quaternary organic base salt of a depolymerized-LMW-epiK5-N-sulfate containing 40%-60% iduronic units with a sulfation agent under O-oversulfation conditions to obtain a depolymerized-LMW-epiK5-amine-O-oversulfate, (b) submitting the depolymerized-LMW-epiK5-amine-O-oversulfate thus obtained to a selective O-desulfation to obtain a depolymerized-LMW-epiK5-amine-O-sulfate, (c) treating a tertiary or quaternary organic base salt of the depolymerized-LMW-epiK5-amine-O-sulfate thus obtained with a O-sulfation agent to obtain a depolymerized-LMW-epiK5-amine-O-sulfate containing at least 80% 6-O-sulfate, and (d) submitting the depolymerized-LMW-epiK5-amine-O-sulfate containing at least 80% 6-O-sulfate thus obtained to a N-sulfation reaction and isolating the depolymerized-LMW-epiK5-N,O-sulfate thus obtained;

wherein (a) comprises (a1) treating a depolymerized-LMW-epiK5-N-sulfate, in acidic form, with a tertiary or quaternary organic base for 30-60 minutes, maintaining the pH at about 7 by addition of the tertiary or quaternary organic base, and isolating an organic base salt of the depolymerized-LMW-epiK5-N-sulfate and (a2) treating the organic base salt of the depolymerized-LMW-epiK5-N-sulfate with an O-sulfation agent under O-oversulfation conditions and isolating the depolymerized-LMW-epiK5-amine-O-oversulfate.

2. The process according to claim 1, wherein the depolymerized-LMW-epiK5-N,O-sulfate thus obtained is isolated as the sodium salt thereof which is optionally converted into another pharmaceutically acceptable salt thereof.

3. The process according to claim 2, wherein said other salt is that with another alkaline metal, an alkaline-earth metal, aluminum or zinc.

4. The process according to claim 1, wherein the starting depolymerized-LMW-epiK5-N-sulfate is obtained by submitting a K5-N-sulfate, in any order, (i) to C5-epimerization with a D-glucuronyl C5-epimerase isolated, purified and either in solution or immobilized on a solid support, at a pH of approximately 7, at a temperature of approximately 30° C. and for a time period of 12-24 hours in the presence of at least one bivalent ion selected among calcium, magnesium, barium and manganese; and (ii) to a nitrous depolymerization followed by reduction, normally with sodium borohydride.

5. The process according to claim 4, wherein the starting depolymerized-LMW-epiK5-N-sulfate is obtained according to the sequence (i)-(ii) and has a mean molecular weight of from about 1,500 to about 12,000.

6. The process according to claim 5, wherein, said mean molecular weight is from about 1,500 to about 7,500.

7. The process according to claim 4, wherein the starting depolymerized-LMW-epiK5-N-sulfate is obtained according to the sequence (ii)-(i) and has a mean molecular weight of from about 4,000 to about 12,000.

8. The process according to claim 7, wherein said molecular weight is of from about 5,000 to about 7,500.

9. The process according to claim 1, wherein the starting depolymerized-LMW-epiK5-N-sulfate consists of a mixture of chains in which at least 90% of said chains has the formula I

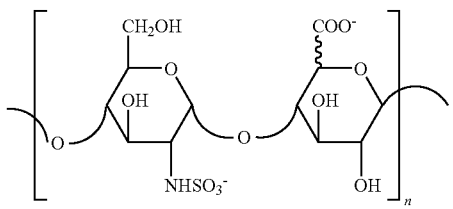

in which 40%- 60% of the uronic units are those of iduronic acid, n is a integer from 2 to 20 and the corresponding cation is chemically or pharmaceutically acceptable.

10. The process according to claim 1, wherein said starting depolymerized-LMW-epiK5-N-sulfate consists of a mixture of chains in which the preponderant species has the formula I'a

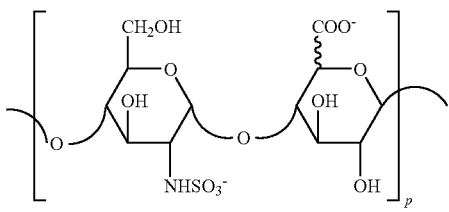

wherein 40% to 60% of the uronic units are those of iduronic acid and p is an integer from 4 to 8.

11. The process according to claim 1, wherein said starting depolymerized-LMW-epiK5-N-sulfate presents a 2,5-anhydromannitol unit of structure (a)

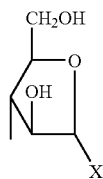

in which X represents a hydroxymethyl group, at the reducing end of the majority of the chains in said mixture of chains.

12. The process according to claim 9, wherein said starting depolymerized-LMW-epiK5-N-sulfate consists of a mixture of chains in which the preponderant species has the formula I'b

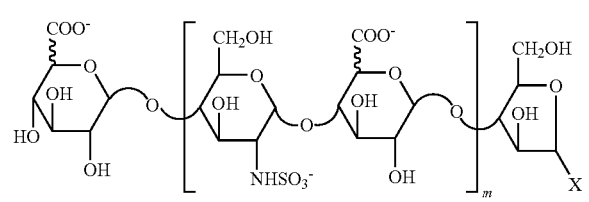

in which X hydroxymethyl, m is 4, 5 or 6, the corresponding cation is a chemically or pharmaceutically acceptable ion and the glucuronic and iduronic units are present alternately, the non reducing extremity being a glucuronic or iduronic unit, with a ratio glucuronic/iduronic from 45/55 to 55/45.

13. A depolymerized-LMW-epiK5-N,O-sulfate containing 40%-60% iduronic units, containing at least 40% 3-O-sulfate groups in glucosamine units, having a sulfation degree of from 2.3 to 2.9 and characterized by the structure (a')

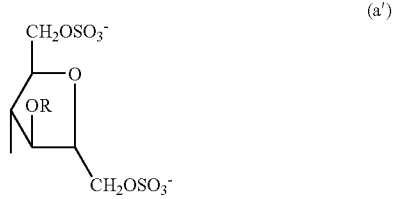

in which R represents hydrogen or $SO_3^-$ at the reducing end of the majority of its chains, obtainable according to a process which comprises
  (a) treating a tertiary or quaternary organic base salt of a depolymerized-LMW-epiK5-N-sulfate containing 40%-60% iduronic units with a sulfation agent under O-oversulfation conditions to obtain a depolymerized-LMW-epiK5-amine-O-oversulfate,
  (b) submitting the depolymerized-LMW-epiK5-amine-O-oversulfate thus obtained to a selective O-sesulfation to obtain a depolymerized-LMW-epiK5-amine-O-sulfate,
  (c) treating a tertiary or quaternary organic base salt of the depolymerized-LMW-epiK5-amine-O-sulfate thus obtained with a O-sulfation agent to obtain a depolymerized-LMW-epiK5-amine-O-sulfate containing at least 80% 6-O-sulfate, and
  (d) submitting the depolymerized-LMW-epiK5-amine-O-sulfate containing at least 80% 6-O-sulfate thus obtained to a N-sulfation reaction and isolating the depolymerized-LMW-epiK5-N,O-sulfate thus obtained;
wherein (a) comprises
  (a1) treating a depolymerized-LMW-epiK5-N-sulfate, in acidic form, with a tertiary or quaternary organic base for 30-60 minutes, maintaining the pH at about 7 by addition of the tertiary or quaternary organic base, and isolating an organic base salt of the depolymerized-LMW-epiK5-N-sulfate and
  (a2) treating the organic base salt of the depolymerized-LMW-epiK5-N-sulfate with an O-sulfation agent under O-oversulfation conditions and isolating the depolymerized-LMW-epiK5-amine-O-oversulfate.

14. A depolymerized-LMW-epiK5-N,O-sulfate containing at least 40% 3-O-sulfate groups in glucosamine units, having a sulfation degree of from 2.3 to 2.9, a mean molecular weight of from about 1,500 to about 12,000 and, at the reducing end of the majority of its chains, the structure (a')

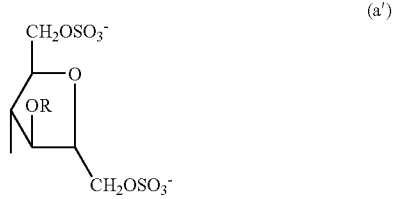

in which R represents hydrogen or $SO_3^-$, or a pharmaceutically acceptable salt thereof.

15. The depolymerized-LMW-epiK5-N,O-sulfate according to claim 14, having a mean molecular weight of from about 1,500 to about 8,000 and a sulfation degree from 2.5 to 2.9.

16. The depolymerized-LMW-epiK5-N,O-sulfate according to claim 15, having a sulfation degree of from 2.7 to 2.9.

17. The depolymerized-LMW-epiK5-N,O-sulfate according to claim 16, having a mean molecular weight of about 6,000.

18. The depolymerized-LMW-epiK5-N,O-sulfate according to claim 14, having a mean molecular weight of about 6,000, a sulfation degree of from 2.7 to 2.9, a content of 80%-95% in glucosamine 6-O-sulfate, of 95%-100% in glucosamine N-sulfate, of 45%-55% in glucosamine 3-O-sulfate, of 35%-45% in glucuronic acid 3-O-sulfate, of 15%-25% in iduronic acid 2-O-sulfate, or a pharmaceutically acceptable salt thereof.

19. The depolymerized-LMW-epiK5-N,O-sulfate according to claim 14 consisting of a mixture of chains in which at least 80% of said chains has the formula III

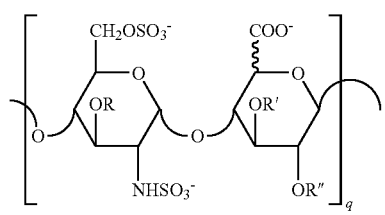
(III)

wherein the 40%-60% of the uronic units are those of iduronic acid, q is an integer from 2 to 17, R, R' and R" are hydrogen or $SO_3^-$ for a sulfation degree of from 2.3 to 2.9, and the reducing end of the majority of the chains in said mixture of chains presents a sulfated 2,5-anidromannitol unit of structure (a')

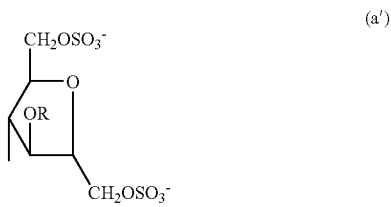
(a')

in which R represents hydrogen or $SO_3^-$ and the corresponding cation is chemically or pharmaceutically acceptable.

20. The depolymerized-LMW-epiK5-N,O-sulfate according to claim 19, consisting of a mixture of chains in which at least 80% of said chains has the formula III wherein q is an integer from 2 to 14.

21. The depolymerized-LMW-epiK5-N,O-sulfate according to claim 19, consisting of a mixture of chains in which at least 80% of said chains has the formula III wherein q is an integer from 2to 11.

22. The depolymerized-LMW-epiK5-N,O-sulfate according to claim 19, consisting of a mixture of chains in which the preponderant species is a compound of formula III wherein q is 8 or 9, R is 45%-55% $SO_3^-$, R' is 35%-45% $SO_3^-$ in glucuronic acid, R" is 15%-25% $SO_3^-$ in iduronic acid, for a sulfation degree of from 2.7 to 2.9.

23. A pharmaceutical composition comprising, as an active ingredient, a pharmacologically active amount of a depolymerized-LMW-epiK5-N,O-sulfate according to claim 13, or of a pharmaceutically acceptable salt thereof, in admixture with a pharmaceutical carrier.

24. The depolymerized-LMW-epiK5-N,O-sulfate according to claim 13, wherein the depolymerized-LMW-epiK5-amine-O-oversulfate contains from 50%-80% 3-O-sulfate groups in the glucosamine units.

25. The process according to claim 1, wherein the depolymerized-LMW-epiK5-amine-O-oversulfate contains from 50%-80% 3-O-sulfate groups in the glucosamine units.

\* \* \* \* \*